United States Patent [19]

Moss et al.

[11] 4,260,490

[45] Apr. 7, 1981

[54] BIOMONITOR TO SAFEGUARD WATER PURIFICATION PROCESS FROM TOXICANTS

[75] Inventors: Jack R. Moss, Charleston, W. Va.; John W. Sugar, Clarence, N.Y.; Ronald A. Riemer, Indianapolis, Ind.; Charles E. Frick, South Charleston; Ronald D. Dillon, Charleston, both of W. Va.

[73] Assignee: Union Carbide Corporation, New York, N.Y.

[21] Appl. No.: 93,039

[22] Filed: Nov. 9, 1979

Related U.S. Application Data

[63] Continuation of Ser. No. 946,312, Sep. 27, 1978, abandoned, which is a continuation of Ser. No. 662,737, Mar. 1, 1976, abandoned.

[51] Int. Cl.$^3$ .............................................. C02F 3/02
[52] U.S. Cl. .................................... 210/620; 210/85; 210/96.1; 210/195.3; 210/220
[58] Field of Search ....................... 210/3, 6, 7, 15, 85, 210/86, 96.1, 97, 103, 104, 195.3, 220; 435/29, 30, 32, 289, 291; 73/19; 422/79, 906

[56] References Cited

U.S. PATENT DOCUMENTS

| | | | |
|---|---|---|---|
| 3,155,609 | 11/1964 | Pampel | 210/3 |
| 3,249,403 | 5/1966 | Bochinski | 23/253 R |
| 3,510,407 | 5/1970 | Stack | 23/230 R |
| 3,542,515 | 11/1970 | Scott | 23/230 R |
| 3,596,767 | 8/1971 | Antonie | 210/96 |
| 3,679,053 | 7/1972 | Koulovato | 210/104 |
| 3,684,702 | 8/1972 | Hartman | 23/230 R |
| 3,731,522 | 5/1973 | Mikesell | 23/230 R |
| 3,740,320 | 6/1973 | Arthur | 23/230 R |
| 3,920,550 | 11/1975 | Farrell | 210/104 |
| 3,986,932 | 10/1976 | Brushwylers | 195/117 |

OTHER PUBLICATIONS

Zeitoun, Optimizing a Petrochemical Waste Bio-Oxidation System Through Automation and Biological Inhibitor Detector, EPA Grant No. S 800 766, pp. 11-17, 95-137.

*Primary Examiner*—Ernest G. Therkorn
*Attorney, Agent, or Firm*—Gary L. Wamer

[57] ABSTRACT

Method of and apparatus for monitoring a waste influent stream to a waste treatment biological basin which contains active microorganisms for levels of materials that are toxic or otherwise injurious to the microorganisms in the basin involving the (a) measurement of the rate of oxygen uptake, R, in a first sample of mixed liquor from said basin, the first sample having a predetermined volume and a predetermined dissolved oxygen content; (b) measurement of the rate of oxygen uptake, M, in a mixture of a second sample of mixed liquor taken from said basin and a sample of liquid from said waste influent stream, the second sample of mixed liquor having substantially the same volume and dissolved oxygen content as said first sample; (c) computation of the differential, $M-R$; (d) provision of a toxic condition signal when said differential, $M-R$, is lower than a predetermined value indicating a toxic effect of the influent stream sample on the sample of mixed liquor from the basin; and/or provision of an undue oxygen depletion signal when the differential, $M-R$, is higher than a predetermined value indicating an amount of highly degradable material in the influent stream capable of causing undue oxygen depletion and bulking and loss of microorganisms in the final clarifier effluent; (e) diverting said influent stream to a holding zone separate from said basin when said toxic condition signal or undue oxygen depletion is indicated.

26 Claims, 18 Drawing Figures

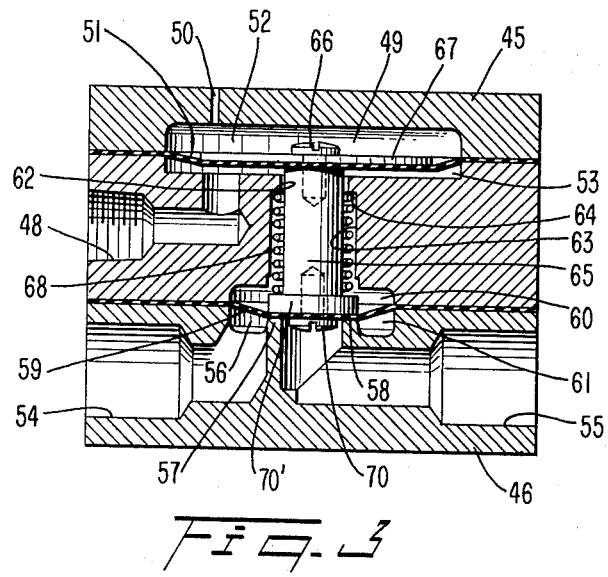
Fig. 3
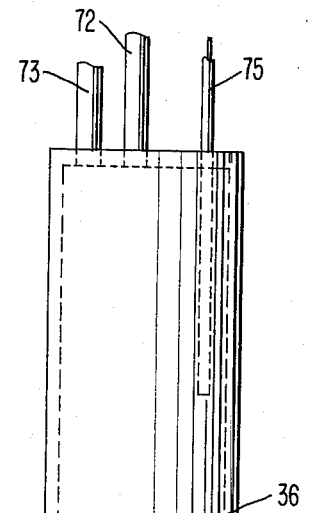
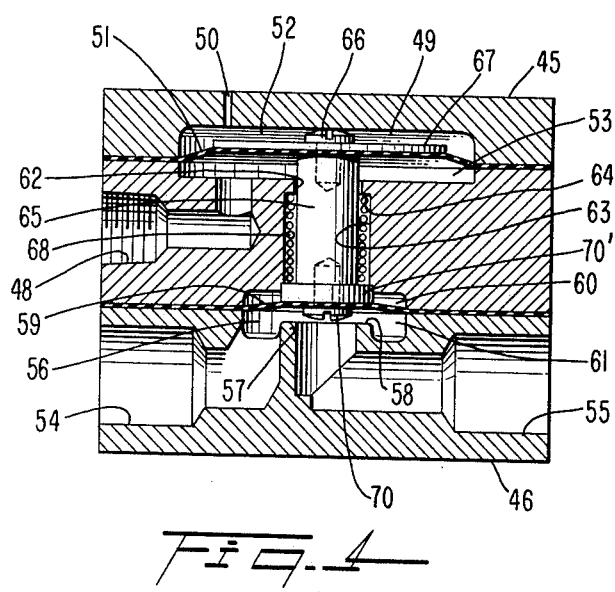
Fig. 4
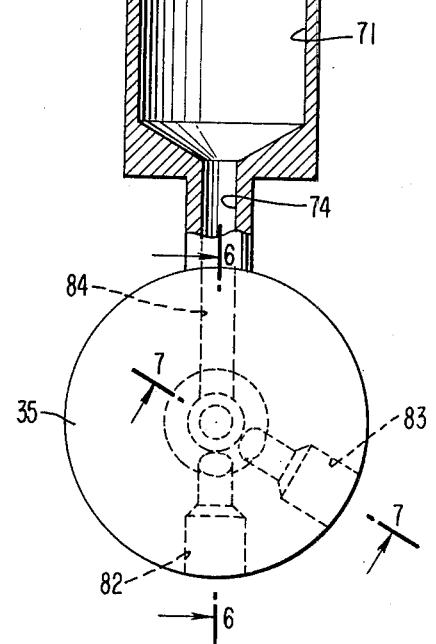
Fig. 5

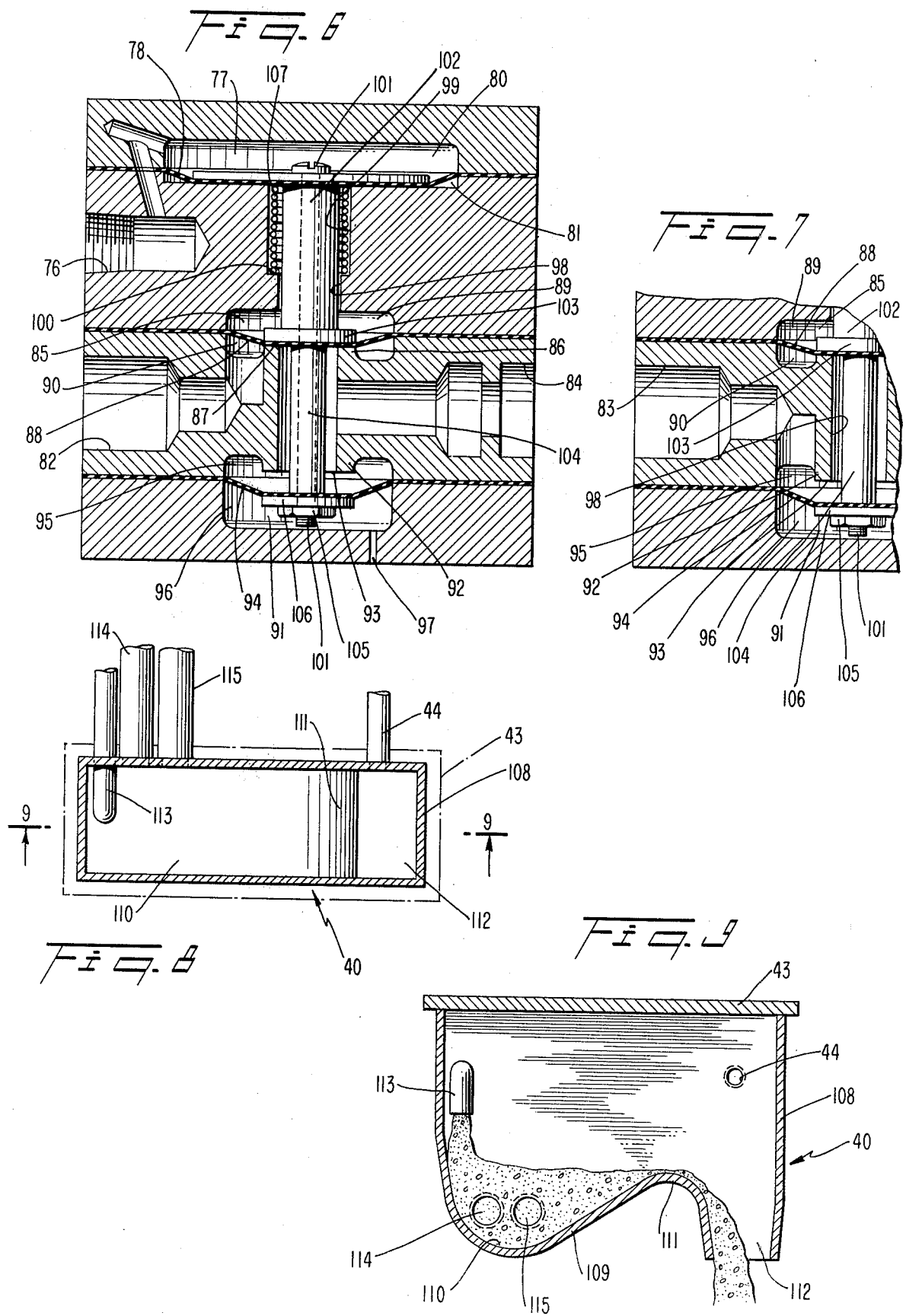

BIOMONITOR TO SAFEGUARD WATER PURIFICATION PROCESS FROM TOXICANTS

This application is a continuation of our prior U.S. application Ser. No. 946,312, filed Sept. 27, 1978, which is a continuation of application Ser. No. 662,737, filed Mar. 1, 1976, both now abandoned.

BACKGROUND OF THE INVENTION

1. Field Of The Invention

The invention relates to a method of and apparatus for monitoring waste influent streams to a secondary treatment biological basin containing active microorganisms to determine whether or not such influent streams contain levels of materials that are injurious to the microorganisms in the biological basin in ample time to take preventive measures to avoid substantial damage to the vitality of the active microorganisms in the basin. The method and apparatus of this invention directly compare the actual effect of a sample of the waste influent on the oxygen uptake of a sample of mixed liquor taken from the biological basin against the oxygen uptake of a control sample of mixed liquor taken from the biological basin and indicate the presence of materials toxic to the active microorganisms or the presence of highly degradable materials that can cause undue oxygen depletion and thus injury to the active microorganisms or a reject signal in the event of a malfunction or error.

2. Description Of The Prior Art

Biological waste treatment involves the oxidation of chemical compounds by active microorganisms to innocuous end products. Both the rate and the extent of oxidation are dependent upon the "health" of the microorganisms and the various properties of the influent waste. A common method for treating sewage to remove pollutants is by the activated sludge process. According to this process, the sewage, with or without primary clarification, is thoroughly mixed with oxygen-containing gas in the presence of aerobic bacteria in a basin of active microorganisms commonly called a secondary treatment basin. The organic matter contained in the sewage is absorbed and biologically oxidized by the bacteria. Subsequently, the bacteria are separated, e.g., by gravity settling, the purified effluent is decanted and discharged into a receiving stream or body of water with or without prior disinfection with chlorine or ozone.

The problems encountered in treating industrial wastes are more complex, especially in the secondary treatment, than with domestic wastes. Many synthetic industrial compounds produced by process units are inhibitory to the respiration of the biological microorganisms in the secondary waste treatment units. Therefore, a method of detecting potentially inhibitory conditions before the waste reaches the secondary unit is needed to protect the microorganisms in the secondary treatment units from large concentrations of highly toxic materials. Of equal importance, detection of highly degradable materials that can cause oxygen depletion in secondary biological basins is needed to prevent bulking and loss of the microorganisms in the final clarifier effluent. Control of these potential upsets is required to avoid severe damage to the secondary treatment basin, to avoid pollution of the stream or body of water receiving the effluent from the secondary treatment basin, and so that the treatment plant can conform to public waterway discharge permits. Inhibitory materials can either be low to high concentrations of potentially toxic compounds or high concentrations of readily degradable organic compounds. In the case of inhibitory toxic compounds, a percentage of the biological organisms are killed, thus reducing the efficiency of the secondary biological waste treatment or even rendering it ineffective. Readily degradable organics, on the other hand, can cause oxygen starvation and depletion in the biological basins, resulting in lowered efficiency and a loss of microorganisms from the final clarifiers because they will not settle out and are carried away with the effluent.

Previously, the secondary treatment unit was protected by detection systems inside the primary treatment boundaries. Many abnormal influent waste conditions were detected too late for correction or diversion. Commercially available oxygen uptake monitors are typically installed in the biobasin and measure the respiration of the biomass after influent waste water has been pumped into the aerobic biological basin. No positive corrective measures can be initiated at this point and it is usually too late to avoid damage and loss. Examples of prior art which measure the respiration of the biomass after the influent waste water has been pumped into the aerobic biological basin include U.S. Pat. Nos. 3,342,727; 3,348,409; 3,426,899; 3,510,407; 3,557,954; 3,731,522 and 3,740,320. U.S. Pat. No. 3,684,702 discloses a method and apparatus for determining the biochemical decomposability of sewage wherein various combinations of sewage and activated sludge are diluted with water and analyzed for BOD to determine the amount of activated sludge to be recycled to the aerating tank to provide optimum decomposition. This patent also describes a laboratory technique for determining toxic sewage waters wherein one analysis fermenter is continually supplied with sewage water, bacteria and additional nutrient while a second analysis fermenter contains only bacteria and the additional nutrient. If the oxygen consumption per time unit is smaller in the first fermenter than in the second, an impediment or poisoning of the bacteria is stated to exist. The different consumptions of oxygen can be utilized for releasing an alarm installation or for indicating countermeasures.

No prior art is known which discloses, teaches or suggests a method of or apparatus for measuring the actual effect of incoming sewage on mixed liquor obtained from the biological basin or lagoon of a secondary treatment unit before it enters the basin.

SUMMARY OF THE INVENTION

The present invention provides an instrument and method that will detect the above-mentioned abnormal conditions in the influent waste stream to a waste treatment plant. In one embodiment, the instrument will automatically sample the influent waste stream, inject an aliquot of this sample into a respirometer filled with mixed liquor from the secondary treatment basin and record the differential oxygen uptake between an unseeded control respirometer containing activated sludge taken from the basin and the waste sample seeded respirometer. Oxygen uptake limits, high and low, can be preset which will sound alarms and/or activate diversion valves to prevent the abnormal wastes in the influent stream from entering the treatment plant.

In an aerobic biological system, the measurement of oxygen uptake with a respiration cell can provide reliable data on the treatability of a specific waste. The biological monitor of this invention incorporates a dissolved oxygen sensing element within the respiration cell to measure the change in dissolved oxygen content during the time in which the chemical compounds are being oxidized by the microorganisms.

The biological monitor of this invention functions well as an extension of the secondary waste treatment unit to give an early warning of abnormal influent waste water conditions. In one embodiment, the instrument works as follows: First, two glass respirometers are filled with mixed liquor (activated sludge) (biomass) pumped from the biological basin. Air is then sparged through the mixed liquor while mixing continuously. After the mixed liquor has been aerated to a near saturation level of dissolved oxygen, the air is shut off and a predetermined volume of the influent waste water is injected into the measuring respirometer. The sample of influent and mixed liquor is continuously mixed to ensure good oxygen contact between the chemicals contained in the influent waste water and the biomass of the mixed liquor. Two dissolved oxygen detectors simultaneously monitor the oxygen content, comparing the respiration of the measuring biomass (injected with influent waste water) against the respiration of the control biomass (no injection). The oxygen uptake rate in the measuring biomass will be dependent upon the relationship between the chemicals in the influent waste water and the oxidation rate characterized by the microorganisms. If the chemicals can be easily degraded by the microorganisms, the dissolved oxygen uptake rate will be comparatively high; however, if the chemicals are inhibitory or toxic to the microorganisms, the oxygen uptake rate will be equal to or less than that measured in the reference respirometer. If the influent waste water contains excessively high concentrations of highly degradable organic chemicals, the measuring respirometer uses significantly more oxygen indicating a significantly higher oxygen uptake rate than the control respirometer.

The instrument is preferably used as an extension of the secondary waste treatment unit to give early warning of any abnormal condition in the influent waste water. This can be done by installing the instrument near the aerobic biobasin of the waste treatment plant and continuously supplying the instrument with mixed liquor from the biobasin and waste water from a point far enough upstream of the waste treatment plant influent to provide ample time to carry out the operation of the apparatus and method of this invention and take corrective action, for example, by diverting the waste water stream to a holding ("panic") pond or container for further analysis and appropriate disposition. Diversion to a "panic" pond allows operating personnel time to make a decision as to proper treatment of the abnormal influent waste water. In the meantime, supplementary instrumentation (e.g., Total Carbon Analyzer, Specific Organic Analyzer, etc.) would permit rapid tracing of the problem back to a specific process unit. The invention also includes, if desired, means responsive to the apparatus and method of this invention for diverting the waste water stream to the holding container for as long as the toxic or highly degradable condition exists in the oncoming stream. The potential for upset ordinarily should be detected within 45 to 60 minutes up to two hours which is the approximate time usually required for primary treatment. Additional reaction time is provided by the time required for travel of the waste water from the sampling point to the primary treatment stage. Diversion can be accomplished before or after primary treatment, more time for detection and diversion being provided if diversion is accomplished after primary treatment.

An advantageously capability of the apparatus and method of this invention is the rapidity with which the analysis of the waste water can be performed. For example, the complete cycle of analysis and set-up for the next cycle can take place in eleven to twenty minutes, although the complete cycle can be accomplished in more or less time. The instrument and method can be operated automatically or manually, as desired. Automatic operation facilitates monitoring the waste water on a continuous twenty-four hour basis. The instrument also can be operated to provide a record of the analytical results in addition to displaying current findings. Alarm devices are also provided to visually and/or audibly signal abnormal conditions. Additionally, the instrument is accurate, reliable, requires little maintenance and is relatively easy to service.

BRIEF DESCRIPTION OF THE DRAWINGS

FIG. 3 is a cross sectional view of a pneumatic diaphragm valve which can be used in the present invention illustrating the valve in the closed position;

FIG. 4 is a cross sectional view similar to that shown in FIG. 3 showing the valve in the open position;

FIG. 5 is a partly broken away front view of a sample injection unit which can be employed in the apparatus of this invention;

FIG. 6 is a sectional view on line 6—6 of FIG. 5;

FIG. 7 is a sectional view partly broken away taken on line 7—7 of FIG. 5;

FIG. 8 is a plan view of a weir which can be used in the apparatus of this invention.

FIG. 9 is a sectional view taken on line 9—9 of FIG. 8;

DESCRIPTION OF SPECIFIC EMBODIMENTS

Figure 1:
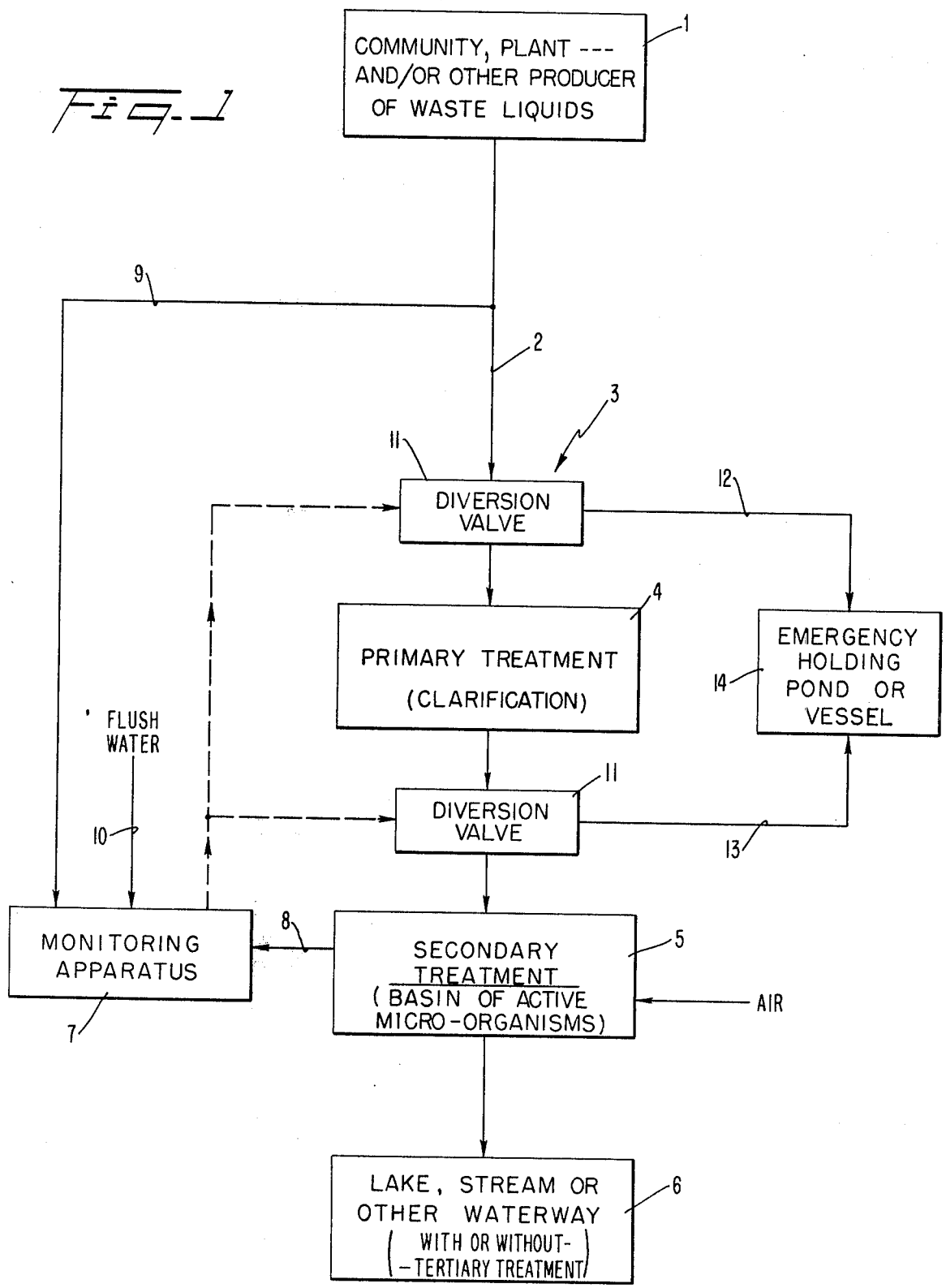
FIG. 1 is a block diagram illustrating a typical sewage treatment plant in which the invention can be used.

FIG. 1 illustrates diagrammatically a type of sewage disposal system wherein waste water from a community or manufacturing plant or both or some other producer of water water 1 is conducted through a conduit 2 to a sewage disposal plant 3 which comprises a primary treatment or clarification stage 4 and a secondary treatment stage 5 where it is aerated while being treated with activated sludge in a basin containing active microorganisms capable of biologically oxidizing the organic matter in the sewage or waste water delivered to the secondary treatment stage. After the secondary treatment stage 5, the effluent can be subjected to treatment with chlorine or ozone or other disinfectant and is released into a lake, stream or other natural waterway 6. In some sewage plants, the effluent from the secondary treatment stage 5 is released directly into the lake, stream or other waterway 6.

The monitoring apparatus (monitor) 7 of the present invention is preferably situated proximate to the secondary treatment stage 5 and draws mixed liquor from the biobasin of the secondary treatment stage 5 through conduit 8. The monitor 7 draws waste water or sewage from conduit 2 via conduit 9 from a point as far upstream as practical. Suitable pumps (not shown) can be used in conduit 9 to deliver the waste water from conduit 2 to the monitor 7 as quickly as possible. The flow rates in conduits 2 and 9 can be regulated such that it is possible to determine the point in time when the portion of waste water from which a particular sample is taken will reach the secondary treatment lagoon 5. The waste water flows continuously in conduit 9 and samples are periodically but continuously analyzed in the monitor 7. Flush water is provided to the monitor 7 through pipe 10 for purposes of cleaning components of the monitor as is explained more fully hereinafter.

There can be provided one or more diversion valves 11 before and/or after the primary treatment stage 5 for directing (when actuated) the flow of waste water through conduits 12 and/or 13 to an emergency holding pond of vessel 14 herein also called a "panic" pond. When a diversion valve 11 is located prior to the primary treatment stage 4, the waste water traveling in conduit 2 is diverted to the "panic" pond 14, when the diversion valve is activated, and does not reach the primary stage 4. The diversion valve 11 when located after the primary stage 4 permits more analysis and reaction time for determining and identifying waste water portions injurious to the active microorganisms in lagoon 5 and actuating the diversion valve 11 to divert the offensive waste water to the "panic" pond 14. Given the flow rates in conduits 2 and 9, the time of arrival of the offensive waste water at the primary and secondary stages 4 and 5 can be predicted. If for some reason time does not permit diversion of the offensive waste water prior to the primary stage 4, it can be accomplished after the primary stage 4 but before the secondary stage 5. It is preferable, however, to divert prior to the primary stage 4 so as to avoid any adverse effect on the primary stage 4 or liquids therein.

Figure 2:
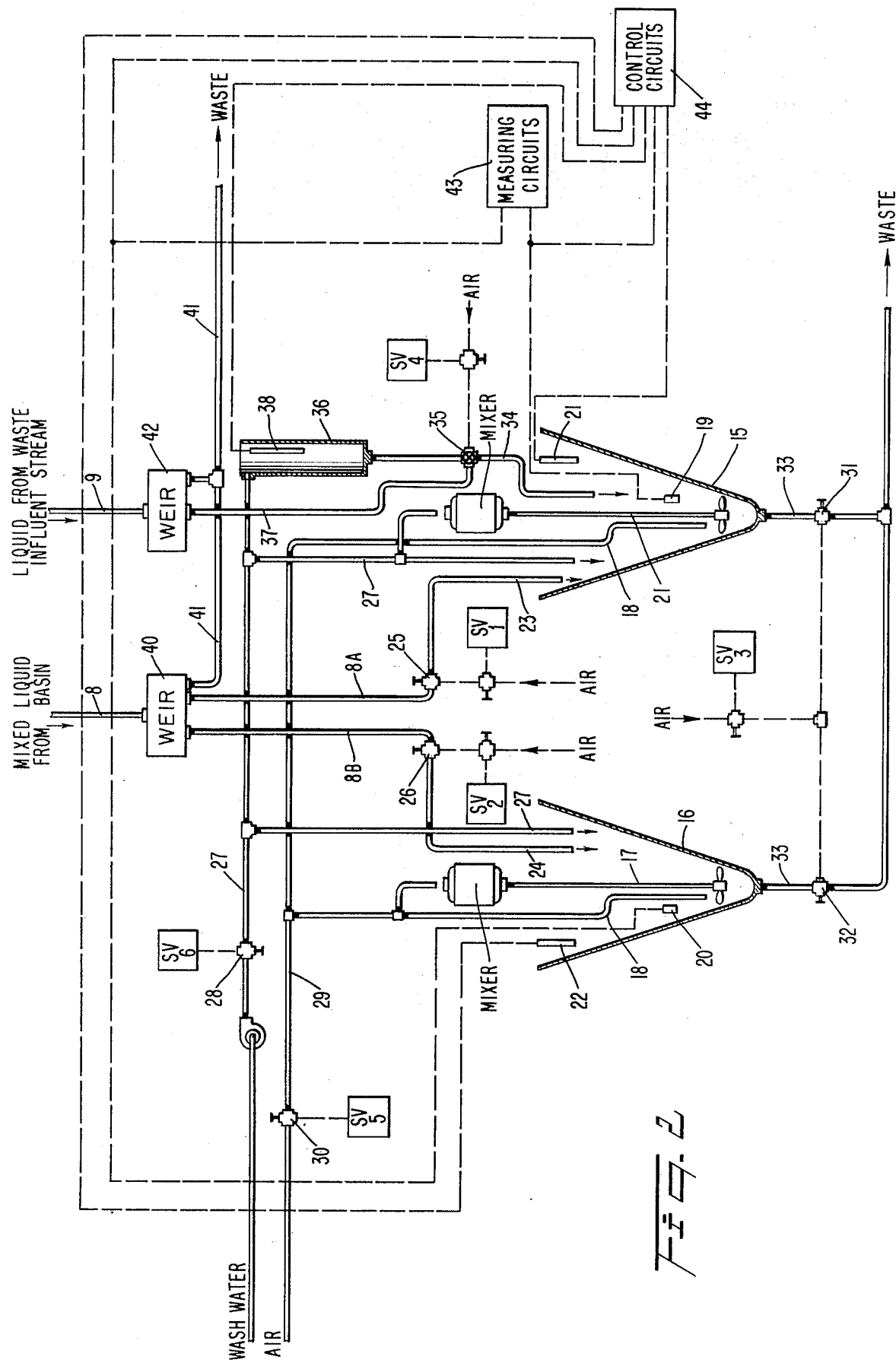
FIG. 2 is a schematic diagram illustrating an embodiment of the apparatus of this invention.

FIG. 2 schematically illustrates one form of the apparatus or monitor 7 of this invention. Monitor 7 utilizes two respirometers, i.e., a measuring respironmeter 15 and a control or reference respirometer 16, each equipped with a stirrer or mixer 17 and an air sparging tube 18. The stirrer 17 can be of any configuration as long as the mixing action produced is efficient and does not draw air into the mixed liquor in the respirometers 15, 16 during operation. Respirometers 15 and 16 are also equipped with dissolved oxygen (D. O.) sensing probes 19 (measuring) and 20 (reference), respectively, and liquid level detecting probes 21 (measuring) and 22 (reference), respectively.

Any suitable D. O. sensing probes 19, 20 can be used. One suitable type has a cathode which is a gold ring imbedded in a lucite block and an anode which is silver recessed in a central well. The interior is filled with an aqueous solution of potassium chloride (KCl). A thin Teflon membrane stretched across the end of the sensor isolates the sensor electrodes from the environment. The membrane is permeable to gases and allows them to enter the interior of the sensor. When a suitable polarizing voltage is applied across the cell, oxygen will react at the cathode causing a current to flow through the cell. The amount of current which flows is proportional to the amount of oxygen to which the membrane is exposed. The sensor in effect measures the oxygen pressure. Since oxygen is consumed at the cathode, it can be assumed that the oxygen pressure inside the membrane is zero. Hence, it can be seen that the force causing oxygen to diffuse through the membrane is proportional to the absolute pressure of oxygen outside the membrane. If the oxygen pressure increases, more oxygen diffuses through the membrane and more current flows through the cell. A lower pressure results in less current. The membrane diffusion is directly proportional to pressure and the oxygen-cell current relationship obeys stoichiometric laws; thus, a linear relationship exists between external oxygen pressure and cell current. The measuring circuit also can be temperature compensated because membrane permeability varies with temperature at a rate of about 4 percent per °C.

The liquid level detecting probes 21, 22 can be of any suitable type although it is preferred that they contain no moving parts and exhibit long term continuous operation capabilities without servicing. A particulary useful type of level detecting probe 21, 22 has a central conductor or wire having an insulating cover, e.g., Teflon, but having its lower end exposed. A positive voltage is applied to the conductor but no current flows until the exposed end is grounded. Provision is made to ground the liquid within the respirometers 15, 16. As shown, the air sparge 18 tubes are made of metal and are grounded. Alternatively, the rod and blades of the stirrers 17 can be grounded or a separate ground can be exposed to the bottom interior of the respirometers 15, 16. The level detecting probes 21, 22 are vertically adjustable to permit the detection of a wide range of liquid levels in the respirometers 15, 16, as desired, and thus provide for a wide range of mixed liquor volumes in the respirometers.

The respirometers 15, 16 are also provided with mixed liquor inlet pipes 23 and 24, respectively, which communicate with a short tube 8A which receives mixed liquor delivered by the conduit 8 from the basin of the secondary treatment stage 5. The inlet pipes 23 and 24 are provided with pneumatically operated valves 25 and 26, respectively, for controlling the amount of mixed liquor flowing into the respirometers 15 and 16, respectively. The valves 25 and 26 are operated by instrument air (15 to 20 psig) which is controlled in each case by solenoid valves SV1 and SV2, respectively, which in turn are actuated in response to signals from the liquid level detector probes 21 and 22, respectively.

Water line 27 is connected to and delivers flush water to each of the respirometers 15, 16 for the purpose of flushing and washing the respirometers after measurements have been made and the contents have been drained. A valve 28 is installed in the flush water line 27 and is actuated by solenoid valve SV6 which in turn is operated in response to a cam timer motor as explained more fully hereinafter. Any low carbon content fresh water supply can be used as flush water. Introduction of the flush water into the respirometers 15, 16 can be accomplished by an efficient jet or jets or manifold.

The air sparge tubes 18 are connected to a source of pressurized air through pipe 29. A valve 30 is located in pipe 29 and is actuated by solenoid valve SV5 which in turn is actuated by the cam timer motor at the proper time to control the passage of air therethrough. The aeration gas can be ambient air or pure oxygen or any synthetic mixture of oxygen in an amount of 20 to 100% with an inert gas so as to simulate the aeration gas actually used in the secondary treatment plant.

At the bottom of the respirometers 15 and 16 are located pneumatically operated drain valves 31 and 32 disposed in drain lines 33 leading from the bottoms of the respirometers to waste disposal. The drain valves 31 and 32 control the draining of the contents of the respirometers and are actuated by instrument air which is controlled by solenoid valve SV3 which in turn is actuated by the cam timer motor at the appropriate point in the cycle.

The measuring respirometer 15 is provided with a waste water sample inlet 34 which communicates through a three-way valve 35 with a volumetric sample measuring cylinder 36. The three-way valve 35 also connects the sample measuring cylinder 36 via short tube 37 with the waste water sample conduit 9. The sample measuring cylinder 36 is provided with a liquid level detecting probe 38 which can be of the same type as probes 21, 22 and which can be adjusted vertically to provide different volumes of samples, as desired. The wash water line 27 also connects into the upper interior part of the measuring cylinder 36 for the purpose of flushing and washing the interior thereof at the appropriate time. The three-way valve 35 is actuated by pressurized instrument air controlled by solenoid valve SV4 which in turn is actuated by the cam timer motor at the appropriate time to admit sample waste water through tube 37 into the sample measuring cylinder 36 to the desired level and, thereafter, to drain the volume of sample in the cylinder 36 to the measuring respirometer 15 through inlet 34.

It is preferred that the ratio of the volume of waste water sample injected into the measuring respirometer 15 to the volume of mixed liquor therein be proportional to the ratio of the actual volume of plant waste water influent flowing into the secondary treatment basin over a given period of time, e.g., one hour, to the actual volume of mixed liquor in the lagoon. Illustratively, the amount of waste water sample injected into the measuring respirometer can amount to about 0.01 to about 0.1 ml, preferably 0.02 to about 0.06 ml, per ml of mixed liquor in the measuring respirometer 15. The microorganisms in the mixed liquor in the measuring respirometer 15, therefore, are subjected to concentrations of the materials present in the waste water influent essentially equivalent to such concentrations as would exist in the secondary treatment basin, if the waste water were allowed to flow into the basin over a given period of time such as one hour.

The mixed liquor conduit 8 is connected to a weir 40 to continuously supply mixed liquor thereto from the secondary treatment basin. Tubes 8A and 8B are also connected to weir 40 to receive mixed liquor therefrom when the respirometers 15, 16 are being filled. The weir 40 is also connected to a drain line 41 for removing unused mixed liquor to waste disposal. As a result the mixed liquor delivered to the respirometers 15, 16 is as fresh as possible, i.e., it is as nearly as possible like the mixed liquor existing in the basin at the time the respirometers are filled. For this reason also it is preferred that the lengths of tubes 8A and 8B from the weir 40 to the valves 25 and 26 and the respirometers 15, 16 be as short as possible.

The waste water conduit 9 is connected to weir 42 to continuously supply waste water thereto. Tube 37 is also connected to weir 42 to receive waste water therefrom when the sample measuring cylinder 36 is being filled. The weir 42 is also connected to drain line 41 for removing unused waste water to waste disposal. As a result the waste water delivered to the cylinder 36 is as fresh as possible. For the same reason, it is preferred that the tube 37 leading from weir 42 to three-way valve 35 and cylinder 36 be as short as possible.

The waste water and mixed liquor from drain lines 33 and 41 normally can be disposed of in the basin of the secondary treatment stage 5. When the waste water has been determined to be injurious to the microorganisms in the basin, it can be dispatched to the "panic" pond 14.

The outputs of the D.O. probes 19 and 20 are connected to measuring circuits 43 for the purpose of determining the oxygen uptakes M and R in the respirometers 15 and 16 and the differential M−R. This output is also used in control circuits 44 for the purpose of initiating and controlling the various functions of the monitor which are more fully explained hereinafter. The outputs of the level detecting probes 21, 22 and 38 also are connected to the control circuits 43 for the purpose of initiating and controlling various functions of the monitor which are more fully explained hereinafter. Alternatively, the ouputs of the D.O. probes 19 and 20 can be read manually and the uptakes M and R and the differential M−R can be computed manually. Also, the various functions such as flushing, draining and filling the respirometers 15 and 16, aerating the contents and drawing the sample and dispatching it to the measuring respirometer 15 can be performed manually in the appropriate sequence. That is, the solenoid valves SV1 through SV6 can be actuated manually in the appropriate sequence.

The pneumatically operated valves 25, 26, 31 and 32 can be of any suitable type available. A particularly useful type developed for use in the monitor of this invention is depicted in FIGS. 3 and 4 which illustrate diametrical cross sections of a diaphragm valve which is cylindrical in shape having substantially flat top and bottom surfaces 45 and 46. FIG. 3 illustrates the valve in closed condition when no air is applied to it and FIG. 4 illustrates the valve in open condition with air under pressure applied to it. The valve has an air inlet port 48 opening into the bottom of a flat cylindrical vented chamber 49 and a vent port 50 extending from the top of chamber 49 to the exterior of the valve. A diaphragm 51 extends across the chamber 49 and is sealed all around to the vertical walls of the chamber dividing the chamber into an upper portion 52 (vented side) and a lower portion 53 (pressure side) which are sealed from each other by the diaphragm 51. The valve is also constructed with a fluid outlet port 54 and a fluid inlet port 55.

Fluid outlet port 54 opens into a second cylindrical chamber 56 (outlet annulus) which is formed with a raised central portion 57, the top surface of which forms a valve seat 58. The fluid outlet port 54 enters the chamber 56 to one side of the raised portion 57 and the fluid inlet port 55 opens into the chamber 56 through the raised portion 57. A second diaphragm 59 extends across the chamber 56 and is sealed to the vertical walls of said chamber dividing it into an upper portion 60 (air side) and a lower portion 61 (fluid side) which are sealed from one another by the diaphragm 59.

The two chambers 49 and 56 are connected by a central bore 62 extending from the bottom center of chamber 49 to the top center of chamber 56. A counter bore 63 concentric with central bore or stem guide 62 extends upwardly from the top of chamber 56 and ends short of chamber 49 to form a ledge or spring seat 64. A pin or stem 65 is secured to the center of diaphragm 51 by means of a screw 66 and a washer or pressure plate 67. The diameter of the pin is sufficiently smaller than the diameter of central bore 62 to permit easy up and down sliding of the pin in the bore and to permit the passage of air between lower portion 53 of chamber 49 and upper portion 60 of chamber 56. A coil spring 68 is disposed in counter bore 63 around pin 65 and is compressed against ledge 64 by washer 67 which is secured to pin 65 by screw 70 which also secures diaphragm 59 to pin 65.

The compression of coil spring 68 normally seals the diaphragm 59 against valve seat 58 to seal the fluid outlet 54 from the fluid inlet 55, the position shown in FIG. 3. When air pressure is applied through air inlet port 48 it exerts upward pressure on diaphragm 51 and when sufficiently great the downward bias of coil spring 68 is overcome and the diaphragm 59 is moved upwardly off of seat 58 to connect the fluid outlet and inlet ports 54 and 55, the position shown in FIG. 4. The pneumatic diaphragm valve shown in FIGS. 3 and 4 and described above are quick acting and reliable and require very little or no maintenance during long term automatic use. The moving parts, i.e., the pin 65 and coil spring 68, are fully protected by diaphragm 59, which is made of chemical resistant elastomer, from the chemicals of the mixed liquor and waste water passing into port 55 through lower chamber 61 and out of port 54.

FIGS. 5, 6 and 7 illustrate the sample measuring cylinder 36 and the three-way valve 35 connected to it. Other devices for measuring out a specified volume of liquid and injecting same into an analytical vessel are available, for example, syringe injection devices, and can be used in place of cylinder 36 and three-way valve 35. The cylinder 36 is formed with a reservoir 71 having a vent 72 and a wash water inlet 73 at the top and a waste water sample inlet-outlet port 74 at the bottom connected to the three-way valve 35. A waste water sample level detecting probe 75, similar to mixed liquor level detecting probes 21 and 22, extends into the reservoir 71 from the top. A three-way valve 35 is formed with a compressed air inlet port 76 opening into a first cylindrical chamber 77. A first diaphragm 78 extends across the chamber 77 and is sealed all around to the vertical walls of the chamber, dividing it into an upper portion 80 and a lower portion 81 which are sealed from each other by diaphragm 78. The air inlet port 76 opens into the upper portion 80 of chamber 77. The valve is also constructed with a waste water inlet port 82, an outlet port 83 leading to the measuring respirometer 15 and an inlet-outlet port 84 which communicates with the inlet-outlet port 74 of the reservoir 71.

As best seen in FIG. 6, waste water inlet port 82 opens into a second cylindrical chamber 85 which is formed with an upwardly extending raised cylindrical portion 86, the top surface of which forms a first valve seat 87. A second diaphragm 88 extends across the second chamber 85 and is sealed all around to the vertical walls of the second chamber dividing it into an upper portion 89 and a lower portion 90 which are sealed from each other by the second diaphragm 88. The waste water inlet port 82 enters the lower portion 90 below second diaphragm 88 to one side of raised portion 86.

As best seen in FIG. 7, outlet port 83 (to respirometer 15) opens into a third cylindrical chamber 91 which is formed with a downwardly extending cylindrical portion 92, the bottom surface of which forms a second valve seat 93. A third diaphragm 94 extends across third chamber 91 and is sealed all around to the vertical walls of the third chamber dividing it into an upper portion 95 and a lower portion 96 which are sealed from each other by the third diaphragm 94. The outlet port 83 enters the upper portion 95 above the third diaphragm 94 to one side of downwardly extending portion 92. An air vent 97 extends from the bottom of the third chamber 91 to the exterior of the valve 35.

The three-way valve 35 is formed with a central bore 98 which extends from the bottom of the first chamber 77 through the second chamber 85 concentric with the first raised portion 86 and first valve seat 87 to the top of the third chamber 91 concentric with the second raised portion 92 and second valve seat 93. A counter bore 99 concentric with central bore 98 extends from the bottom of first chamber 77 and ends short of the second chamber 85 to form a ledge 100.

A bolt 101 extends through the central bore 98 from the first chamber 77 to the third chamber 91. A first sleeve 102 is mounted on the bolt 101 and extends from the lower surface of the first diaphragm 78 to a washer 103 on the upper surface of second diaphragm 88. The diameter of the first sleeve 102 is slightly smaller than the diameter of central bore 98 so that it slides easily in said bore and permits air to be displaced through the space between said sleeve and said bore from the lower portion 81 to the first chamber 77 to the upper portion 89 of the second chamber 85 and back again.

A second sleeve 104 is mounted on the bolt 101 and extends from the lower surface of the second diaphragm 88 to the upper surface of the third diaphragm 94. The diameter of the second sleeve 104 is much smaller than the central bore 98 so as to permit waste water to easily pass through the space between the outer surface of said second sleeve and the walls of said bore from the second chamber 85 to the reservoir outlet-inlet port 84 and from said port to the third chamber 91 depending on the position of the second and third diaphragms 88 and 94. A nut 105 is tightened up on the bolt 101 against washer 106 on the lower surface of the third diaphragm 94 so that all three diaphragms 78, 88 and 94 are interconnected via said bolt and sleeves 102 and 104 and move upwardly and downwardly together.

A coil spring 107 is disposed in counter bore 99 and is compressed between ledge 100 and the lower surface of first diaphragm 78. A washer 108 is mounted on the bolt 101 between its head and the upper surface of first diaphragm 78 to provide a firm support for the upper end of coil spring 107. The compression of coil spring 107 normally forces the bolt 101, sleeves 102 and 104 and the central portions of all three diaphragms upwardly to seal the third diaphragm 94 against second valve seat 93 and thus shut off communication of outlet port 83 (respirometer 15) from the reservoir inlet-outlet port 84 while the second diaphragm 88 is up and away from first valve seat 87 allowing access of waste water from waste water weir 42 through inlet port 82 to reservoir inlet-outlet port 84 allowing the reservoir 71 to fill. When air pressure is applied through air inlet port 76 the bias of spring 107 is overcome forcing the bolt 101, sleeves 102 and 104 and the central portions of all three diaphragms to move downwardly to seal the second diaphragm 88 against the first valve seat 87 and shut off the flow of waste water from waste water weir 42 into the reservoir 71 while the third diaphragm 94 is moved away from the second valve seat 93 allowing the waste water sample in reservoir 71 to flow into respirometer 15.

The solenoid valves SV1 through SV4 are of the type that, when actuated, pressurized air is admitted to the pneumatically operated diaphragm valves 25, 26, 31, 32 and 35 and, when not actuated, the pressurized air in said diaphragm valves is exhausted to enable the bias of the coil springs 68 and 107 to move the respective diaphragms as explained hereinbefore.

FIGS. 8 and 9 illustrate the construction of a preferred form of the mixed liquor weir 40 which is in the form of a rectangular box 108 having a bottom 109 shaped in the form of a trough 110 which rises to a high point 111 and then drops to an outlet port 112 which leads to the drain 41 to waste disposal. The mixed liquor enters through an inlet tube 113 from the conduit 8 from the basin 5. Near the bottom of the trough 110 almost directly under the inlet tube 113, outlet tube 114 passes through the side wall of and opens into the interior of the box 108. Outlet tubes 114 and 115 are connected to tubes 8A and 8B, respectively, leading to the valves 25 and 26, respectively, which feed the mixed liquor to the respirometers 15 and 16, respectively. A vapor tight cover 116 (not shown in FIG. 8) is clamped to the open top of the box 108. A vent tube 117 passes through the side wall of box 108. As shown in FIG. 9, the liquid coming through inlet tube 113 fills the trough 110 and spills over the high point 111. Liquid is drawn out by gravity through outlets 114 and 115 which may temporarily halt the spillover of liquid at high point 111. When sufficient liquid has been drawn off and flow through outlets 114 and 115 is stopped, the liquid builds up in trough 110 and again spills over the high point 111 to drain. The weir 40 can be of any suitable design, although the one depicted in FIGS. 8 and 9 is believed to be optimum.

The waste water sample weir 42 can be similarly constructed except that no outlet ports 114 or 115 are provided. Instead, the waste water from conduit 9 passes through a tee (not shown) before it enters the weir 42 through inlet tube 113. Thus, one leg of the tee is connected to conduit 9 and another to inlet tube 113. The other leg of the tee is connected via tube 37 to the three-way valve 35 at the bottom of the sample measuring cylinder 36. When no sample is being drawn off to the three-way valve 35 via tube 37, it flows into the weir 42 through inlet tube 113, fills the trough 110 and spills over high point 111 and out through the outlet port 112. When waste water is drawn off through tube 37, the flow to the weir 42 essentially stops and spillover essentially ceases until no waste water is drawn off through tube 37. Other designs of weir 42 can be used, although the one described hereinabove is believed to be optimum. Both weirs 40 and 42 and the tee connected to inlet tube 113 of weir 42 are located sufficiently above the respirometers 15 and 16, valves 25 and 26, three-way valve 35 and sample measuring cylinder 36 as to provide easy gravity flow from the former to the latter. The respirometers 15 and 16 are located sufficiently below sample measuring cylinder 36 as to provide easy gravity flow from the cylinder 36 to the respirometers 15, 16.

Figure 10:
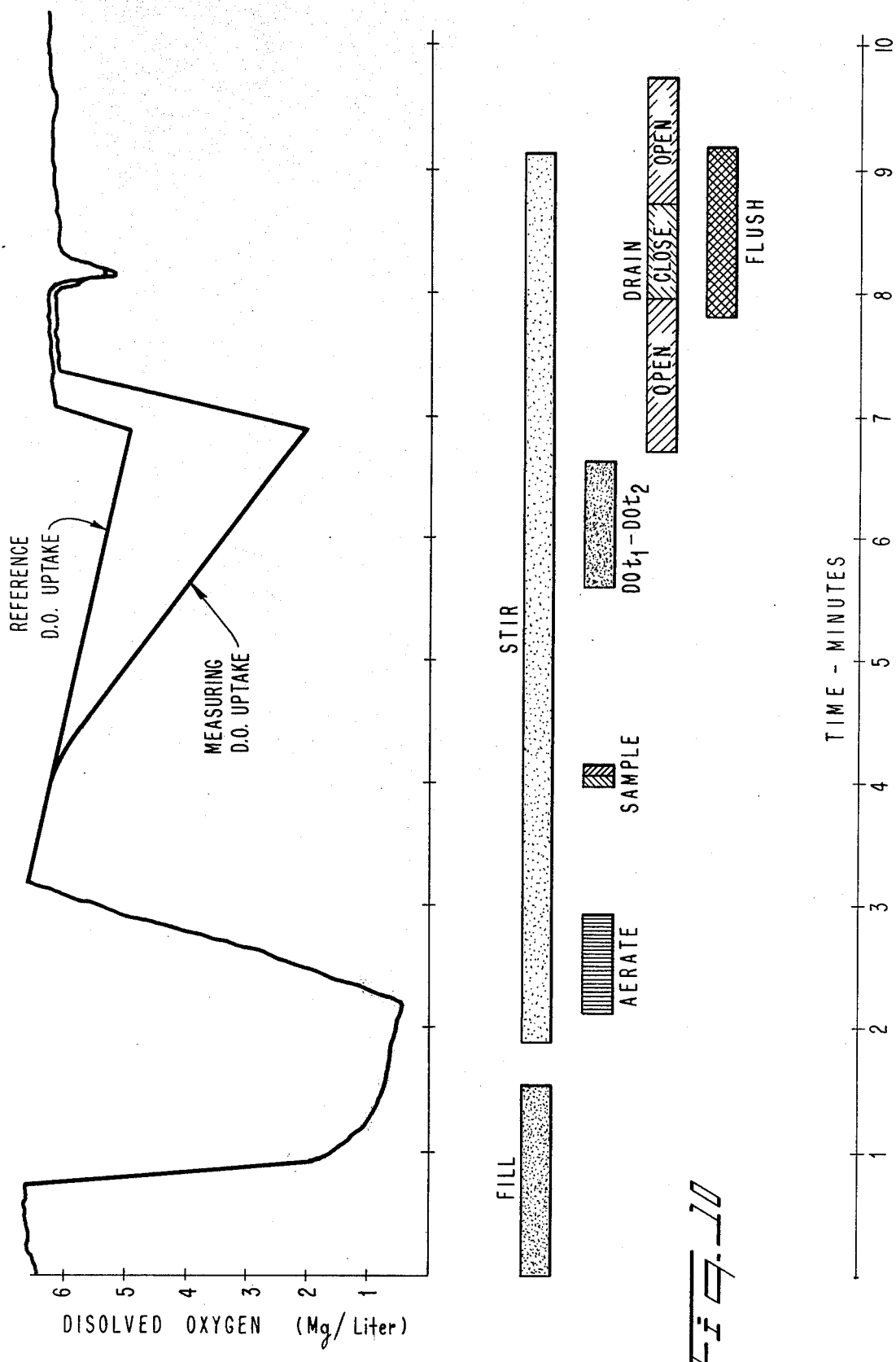
FIG. 10 is a graphical representation of the dissolved oxygen content in the reference and measuring respirometers at various points in the cycle of the apparatus and method of this invention.

FIG. 10 illustrates the actual levels of dissolved oxygen in mg/liter of liquid in the respirometers 15, 16 as detected by the D.O. probes 19, 20 in a typical cycle. The dissolved oxygen values, uptake rates and times are illustrative only and do not limit the flexibility of the monitor of this invention. The upper portion of FIG. 10 is a plot of dissolved oxygen in mg/liter against time in minutes. The lower portion is a block graph illustrating the various functions performed by the monitor during various periods in the cycle. "Fill" designates the filling phase when the respirometers 15 and 16 are filled with mixed liquor from the basin. In the early stages of the "Fill" phase the measured dissolved oxygen was quite high because the D.O. probes 19 and 20 were exposed to air. This condition continued until the mixed liquor in the respirometers reached and covered the D.O. probes whereupon the measured dissolved oxygen dropped precipitously indicating a low amount of dissolved oxygen in the mixed liquor.

The "Stir" phase, i.e., stirring of the mixed liquor in both respirometers, began just prior to the two minute mark and continued to about the nine minute mark.

The "Aerate" phase was started at about the two minute mark and lasted about one minute during which period the mixed liquor was aerated with air through the air sparge tubes 18. The "Aerate" phase increased the measured dissolved oxygen to more than 6 mg/liter. Between the three minute and four minute marks, after aeration, the measured dissolved oxygen dropped off slightly to about 6 mg/liter indicating some oxygen consuming activity in the mixed liquor. Just prior to the four minute mark the "Sample" phase began, that is, the sample measuring cylinder 36 was filled with a waste water sample which was then injected into the measuring respirometer 15 beginning at about the four minute mark. It took only several seconds for the sample to be filled into the measuring cylinder 36 and to be injected from it into the measuring respirometer 15. After injection of the sample into the measuring respirometer 15, the measured dissolved oxygen therein dropped off quite rapidly from about 6 mg/liter at just past the four minute mark to about 2 mg/liter at a point just prior to the seven minute mark whereas the measured dissolved oxygen in the reference respirometer 16 to which no waste water sample was added dropped off to only about 5 mg/liter during the same interval. Over this approximately 2.7 minute interval the oxygen uptake M for the measuring respirometer 15 to which the waste water sample was added is computed to be about 4 mg/liter or 1.5 mg/liter/min whereas the oxygen uptake R for the reference respirometer 16 to which no waste water sample was added is computed to be about 1 mg/liter or about 0.37 mg/liter/min. The differential M−R is computed to be about 3 mg/liter or about 1.13 mg/liter/min.

At about the five and one-half minute mark, $t_1$, the "$DOt_1-DOt_2$" phase began and extended to about the six and one-half minute mark, $t_2$. During this phase, which lasted about one minute, the dissolved oxygen was measured at $t_1$ and at $t_2$ and the uptake $DOt_1$-

—$DOt_2$ was computed for each of the respirometers 15 and 16. For the reference respirometer 16 the uptake $DOt_1 - DOt_2$, or R, was about 0.37 mg/liter/min and for the measuring respirometer 15 the uptake $DOt_1 - DOt_2$ was about 1.5 mg/liter/min. The differential M−R is computed at about 1.13 mg/liter/min. $DOt_1 - DOt_2$ can be measured and computed over any interval between 6 mg/l and 2 mg/l after injection of the waste water sample and before draining since the dissolved oxygen uptake in each respirometer is linear as shown by the plot of the upper portion of FIG. 10.

After the $DOt_1 - DOt_2$ has been determined the drain valves 31 and 32 are opened to empty the respirometers 15 and 16. The D.O. probes 19 and 20 sense the oxygen in the air when the liquid level drops below them and the measured dissolved oxygen increases sharply as shown in FIG. 10. Just before the drain valves 31 and 32 are closed again the wash water valve 28 is opened to flush both respirometers 15, 16 and the measuring cylinder 36. The drain valves 31, 32 are closed for a short period while wash water is still on and then they are opened again while still flushing. Thereafter; the wash water valve 28 is closed and flushing ceases. The drain valves 31, 32 stay open for a short period to allow wash water in the respirometers, 15, 16 and sample measuring cylinder 36 to completely drain and then they close again in readiness for the next cycle.

Oxygen uptake values for normal acceptable conditions, toxic conditions, undue oxygen depletion conditions, i.e., high concentrations of oxygen degradable materials, and reject conditions depend upon the operation parameters of the specific waste treatment facility and the mixed liquor or aerobic activated sludge utilized. For purposes of illustration only, there are listed below representative concentration spans that could be considered typical normal limits and typical alarm limits for oxygen uptake of a particular aerobic activated sludge (mixed liquor) having 3000 to 5000 mg/liter suspended solids and a Total Organic Carbon load of 500 to 5000 mg/liter. The representative limits given below were established empirically from data collected during evaluation of the apparatus and method of this invention at two specific waste treatment facilities.

|  | mg./l./hr. |
|---|---|
| Normal or acceptable oxygen uptake differential (M-R) | 60 to 300 |
| Toxic oxygen uptake differential (M-R) | <20 |
| High oxygen uptake differential (M-R) | >300 |
| Reject oxygen uptake, reference respirometer only (R) | <10 |

These limits or ranges are only representative and could change depending upon the operational parameters of the specific waste treatment facility being monitored by the apparatus and method described herein.

FIGS. 11 through 18 illustrate an automated version of the monitor of this invention where the various functions are carried out automatically. The automatic monitor functions are divided into two major areas: Analysis Setup Electronics and Measurement Electronics. The analysis setup section takes care of all the necessary steps to get ready for the analysis, and the measurement section performs the analysis, displays the results, and controls the alarm outputs.

Referring first to the Analysis Setup Electronics, at the beginning of a cycle, the respirometers 15, 16 must be drained, flushed, filled with flush water, drained again, and then filled with mixed liquor. At this time, the dissolved oxygen level is normally very low, so air is bubbled into the respirometers 15, 16 until each equals or exceeds a preset level (typically near 6 mg/liter). A sample from the influent waste water stream is then added to the measuring respirometer 15. Having completed the above, the respirometers are now ready for the analyses, which are fully described later in the Measurement Electronics Section. The entire setup cycle is timed and sequenced by an eight switch cam timer.

Figure 11:
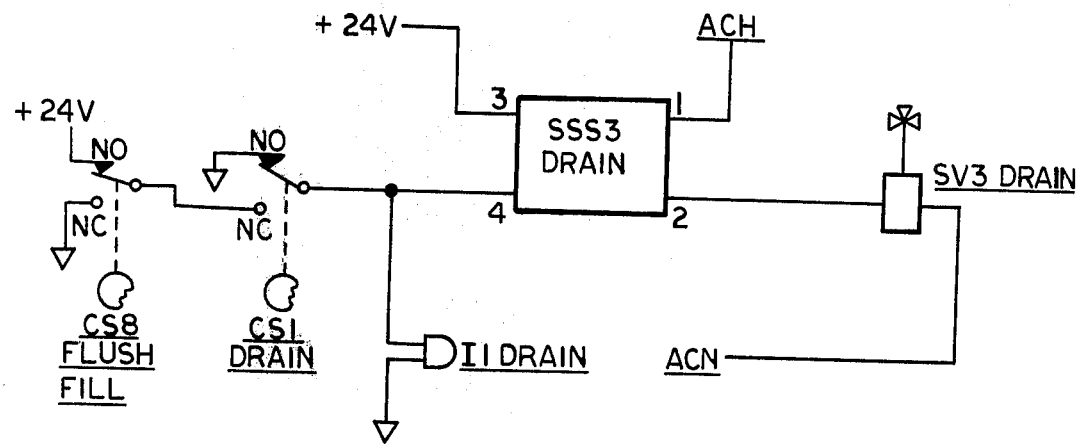
FIG. 11 is a schematic diagram of a respirometer drain control system which can be used in the apparatus of this invention.

FIG. 11 shows that two of the cam switches, CS1 and CS8, are used for draining the respirometers 15, 16. At the beginning of the cycle, CS1 enters its dwell, i.e., valley of the cam, and +24 volts are supplied from the normally open contact N.O. of CS8 through the normally closed NC contact of CS1 to both the drain indicator lamp I1 and solid state switch SSS3. SSS3 has input pin 4 connected to the output of cam switch CS1, input pin 3 connected to +24 volts DC and output pins 1 and 2 in a 120 volt AC circuit and operates as a relay to provide a convenient way to switch 120 volts AC with DC control signals. The ouput pin 1 is connected AC voltage hot, ACH, and the output pin 2 is connected to one lead of solenoid valve SV3. The other lead of solenoid valve SV3 is connected to AC neutral, ACN, so that solid state switch SSS3 controls AC power to SV3. The DC input, i.e., at pins 3 and 4, switches off the output pins 1 and 2, when pin 4 is +24 V. When pin 4 is at ground potential, SSS3 supplies AC power to SV3. The input is optically isolated (coupling by means of an LED-Phototransistor pair), from the output circuit, and the output delays switching on until the next zero crossing of the AC wave form.

When +24 volts is applied to pin 4 of SSS3, its output switches off, removing 120 V AC from solenoid valve SV3, which opens both respirometer drain valves 31 and 32. Later in the cycle, CS8 enters its dwell (while CS1 is still in its dwell) and ground potential (instead of +24 volts) is supplied to pin 4 of SSS3, turning SSS3 on. This applies 120 V AC to solenoid valve SV3 which is thereby activated and closes both respirometer drain valves 31 and 32 and allows the respirometers 15, 16 to fill with flush water. The flush water is turned on by CS2 just before CS8 enters its dwell as is explained more fully hereinafter in reference to FIG. 12. When enough time has elapsed for the respirometers 15, 16 to fill, CS8 will leave its dwell (with CS1 and CS2 still in their dwells) and +24 volts is again applied to pin 4 of SSS3 to switch off its output, thus deactivating solenoid valve SV3 which opens both respirometer drain valves 31, 32. The respirometers again empty. CS2 leaves its dwell to cut off flush water and shortly thereafter, allowing sufficient time to elapse for the respirometers 15, 16 to drain off, CS1 leaves its dwell just prior to the fill cycle. This again supplies ground to pin 4 of SSS3 thereby applying 120 V AC to solenoid valve SV3 which closes both respirometer drain valves 31, 32.

Figure 12:
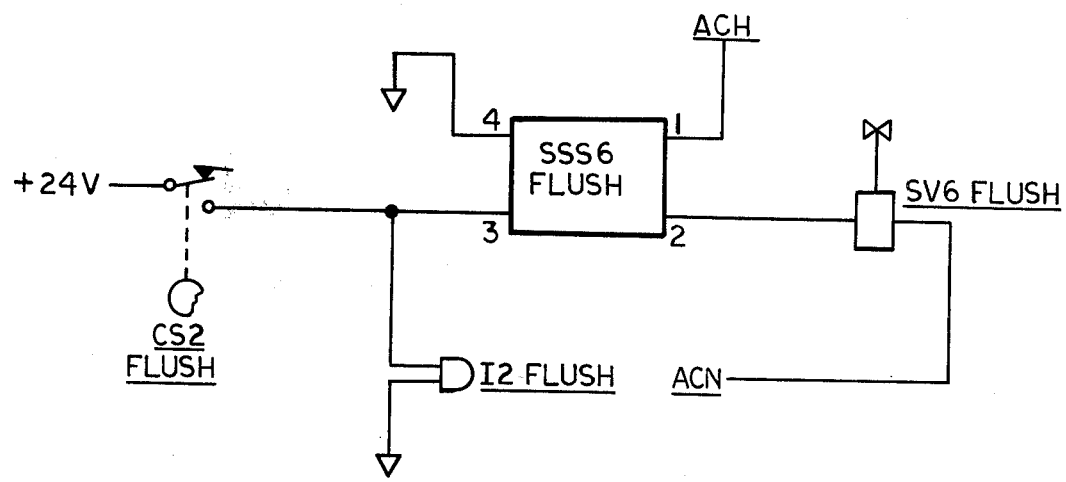
FIG. 12 is a schematic diagram of a respirometer flush control system.

FIG. 12 shows the flush circuits which are controlled by cam switch CS2. When CS2 enters its dwell (just before CS8 does) +24 volts is applied to flush indicator lamp 12 and to pin 3 of solid state switch SSS6 (pin 4 is connected to ground) switching on its output to solenoid valve SV6 energizing it to open flush water valve 28 allowing flush water to enter the respirometers 15, 16. CS2 remains in its dwell until after CS8 has left its dwell. CS2 leaves its dwell before CS1 leaves its dwell. When CS2 leaves its dwell pin 3 of SSS6 is disconnected from +24 volts switching off its output to solenoid valve SV6 which de-energizes and closes flush water valve 28.

Figure 13:
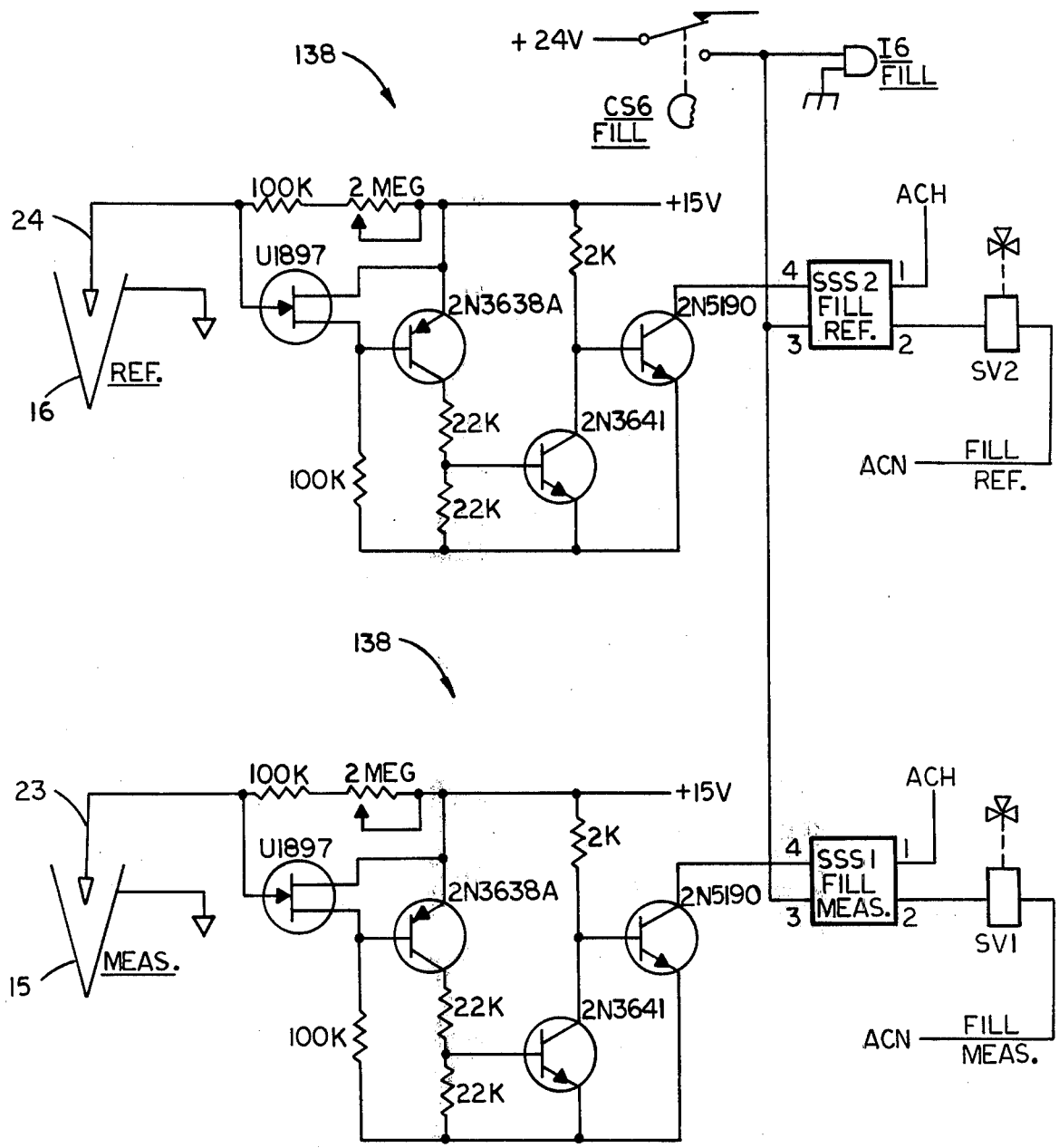
FIG. 13 is a schematic diagram of a respirometer filling control system.

FIG. 13 shows the fill system. At the correct time in the cycle after flush water valve 28 and drain valves 31, 32 have been closed, cam switch CS6 enters its dwell and +24 volts DC is applied to pins 3 of solid state switches SSS1 and SSS2. This switches on the output of SSS1 and SSS2 and energizes indicator lamp 16. Fill valve solenoids SV1 and SV2 are energized and apply air to the fill valve actuators, opening the valves 25 and 26. Each respirometer 15, 16 has a level sensing probe 23, 24 and an electronic circuit 138 as shown in FIG. 13 to sense when the mixed liquor has filled up to the level of the probes 23 and 24.

At the start of the fill cycle, the probes 23 and 24 are out of the liquid and the output transistors of the electronic circuits will be on, thus supplying ground to the other side of the inputs (pins 4) of the solid state switches SSS1 and SSS2 and energizing solenoid valves SV1 and SV2 which open valves 25 and 26 allowing the respirometers to fill. Inside the respirometers 15, 16 a solution ground is achieved through the various metal parts, e.g., the air sparge tube 18 or stirring rod of stirrer 17, and when the liquid reaches the probes 23, 24, a conductive path is created between the probe and ground. The electronic circuits 138 sense this and the output transistors thereof turn off, remove the drives from the solid state switches, SSS1 and SSS2, de-energize the electric solenoid valves SV1 and SV2 and close the associated fill valves 25 and 26 to stop the flow of mixed liquor to the respirometers 15, 16. It will be appreciated that one respirometer may fill to its level detecting probe before the other, in which case, the flow of mixed liquor to it will be cut off while the other respirometer is still completing its fill cycle as described above. Thereafter fill cam switch CS6 leaves its dwell to prepare for the next fill cycle.

Figure 14:
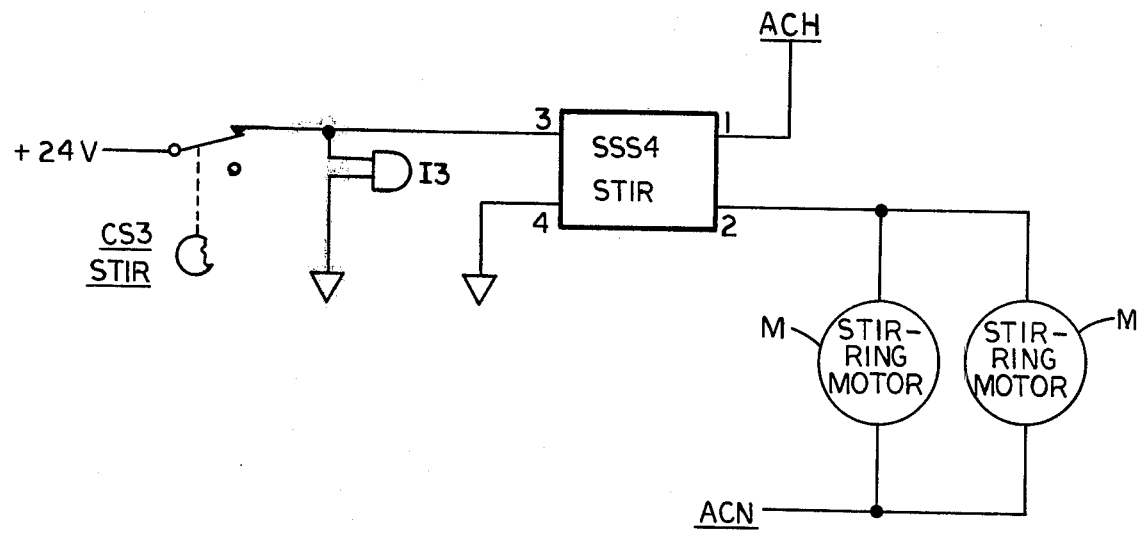
FIG. 14 is a schematic diagram of a respirometer stirring control system.

FIG. 14 illustrates the stir system. When the cam switch CS3 is out of its dwell, +24 volts DC is supplied to the indicator lamp I3 and pin 3 of SSS4, pin 4 being grounded. This completes the connection of the mortor M to ACH (120 V AC) and the motor M runs to provide stirring from a time just prior to aeration to a time just prior to termination of the flush cycle. At the correct time in the cycle, just before cam switch CS2 leaves its dwell to shut off the flush water, cam switch CS3 enters its dwell. This removes the +24 volts DC from the indicator lamp I3 and from pin 3 of solid state switch SSS4 which switches off the 120 V AC to the stirring motor M. Cam switch CS3 remains in its dwell for a period beginning at a point in time after respirometer drain valves 31 and 32 have been closed and the respirometers 15, 16 have been filled with mixed liquor, until just before aeration cam switch CS4 enters its dwell to begin aerating the mixed liquor in the respirometers 15, 16. At this time stir cam switch CS3 leaves its dwell which supplies the drive to SSS4 and energizes stirring motor M to commence stirring the mixed liquor in both respirometers.

Figure 15:
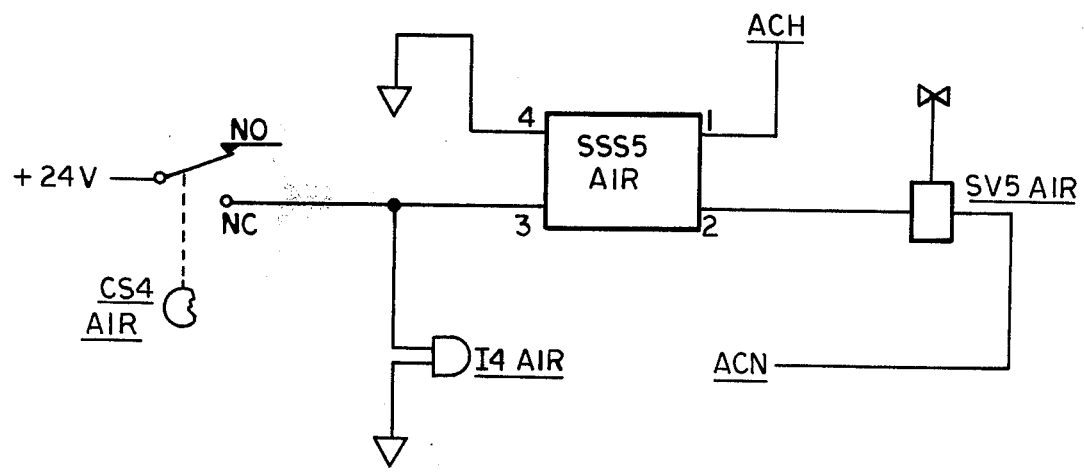
FIG. 15 is a schematic diagram of a respirometer aeration control system.

FIG. 15 illustrates the aeration system which comprises cam switch CS4. At the proper time, after the respirometers 15, 16 have filled and shortly after the stirring motor M is energized, the air cam switch CS4 enters its dwell. This applies +24 volts to indicator lamp I4 and to pin 3 of solid state switch SSS5 (pin 4 of which is grounded) and this switches on 120 V AC to the solenoid valve SV5. This opens air sparge valve 30 and causes air or aerating gas to bubble into the mixed liquor in both respirometers 15 and 16.

Figure 16:
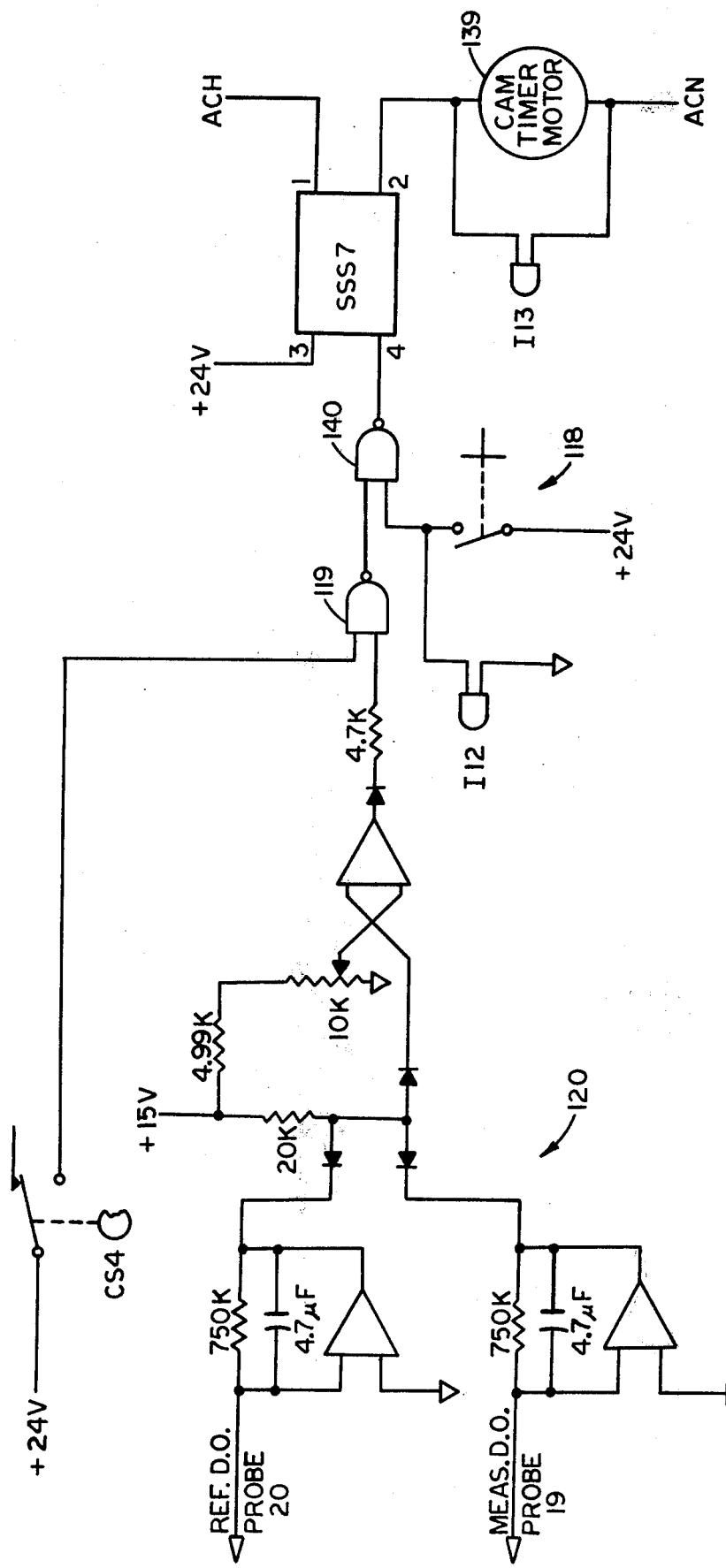
FIG. 16 is a schematic diagram of a cam timer motor control system.

Due to many variables, the length of time required to properly aerate the mixed liquor in both respirometers is unpredictable. To overcome this problem, the dissolved oxygen level of both respirometers 15, 16 is monitored by the aeration level circuit, which is shown in FIG. 16. This circuit turns off the cam timer motor, leaving CS4 in its dwell until the dissolved oxygen in both respirometers 15, 16 has reached at least a minimum level preset in the aeration level circuit. After this level is attained, the cam timer motor is agian turned on by the aeration level circuit shown in FIG. 16 and the cycle continues. This arrangement provides the necessary time for the dissolved oxygen in the mixed liquor in the respirometers 15, 16 to reach the desired level regardless of the length of time to do so. After the cam timer motor has been energized again, the cam switch CS4 leaves its dwell and removes the drive from SSS5. The solenoid valve SV5 is de-energized and closes air sparge valve 30.

The cam timer motor control circuit as shown in FIG. 16 includes a solid state switch SSS7 having its output pin 2 connected to one lead of the cam timer motor 139 and its output pin 1 connected to an AC hot line ACH. The other lead of the cam timer motor is connected to an AC neutral line ACN. Pin 3 of SSS7 is connected to +24 volts DC and pin 4 is connected to an electronic gate 140, one input of which is connected to a +25 volts DC supply through a push on/off switch 118 (cam timer motor enablement switch). The other input of gate 140 is connected to the output of a second electronic gate 119, a first input of which is connected to air cam switch CS4 so that when CS4 is in its dwell +24 volts DC is supplied and when it leaves its dwell the +24 volt DC source is disconnected. A second input of gate 119 is connected to the aeration level circuit 120 which receives the output signals of both the measuring and reference D.O. probes 19 and 20.

When the D.O. level in one or both respirometers 15, 16 is below the setpoint of the aeration level circuit 120 the output thereof to second gat 119 is high and when it reaches or exceeds the setpoint said output is low. The first input to second gate 119 is high when air cam switch CS4 is in its dwell supplying +24 volts DC to gate 119 and low when CS4 is out of its dwell. The output of second gate 119 to first gate 140 is low when the D.O. level is below the setpoint of circuit 120 and CS4 is in its dwell. The input from switch 118 is high when it is on and low when it is off. A low from either input to first gate 140 causes the output of SSS7 to switch off, thus turning off the cam timer motor 139. A high from both inputs to first gate 140 causes the output of SSS7 to switch on thereby turning on the cam timer motor 139. Therefore, the cam timer motor 139 runs (1) when the cam switch CS4 is out of its dwell regardless of the D.O. level in the respirometers 15, 16 and (2) when the cam switch CS4 is in its dwell and the D.O. levels in the respirometers are at or above the setpoint of the aeration level circuit 120. The cam timer motor 139 is stopped only when the cam switch CS4 is in its dwell and the D.O. levels in the respirometers 15, 16 are below the setpoint of the aeration level circuit 120. This allows the attainment of the desired D.O. level in the respirometers 15, 16 regardless of the length of time required.

Figure 17:
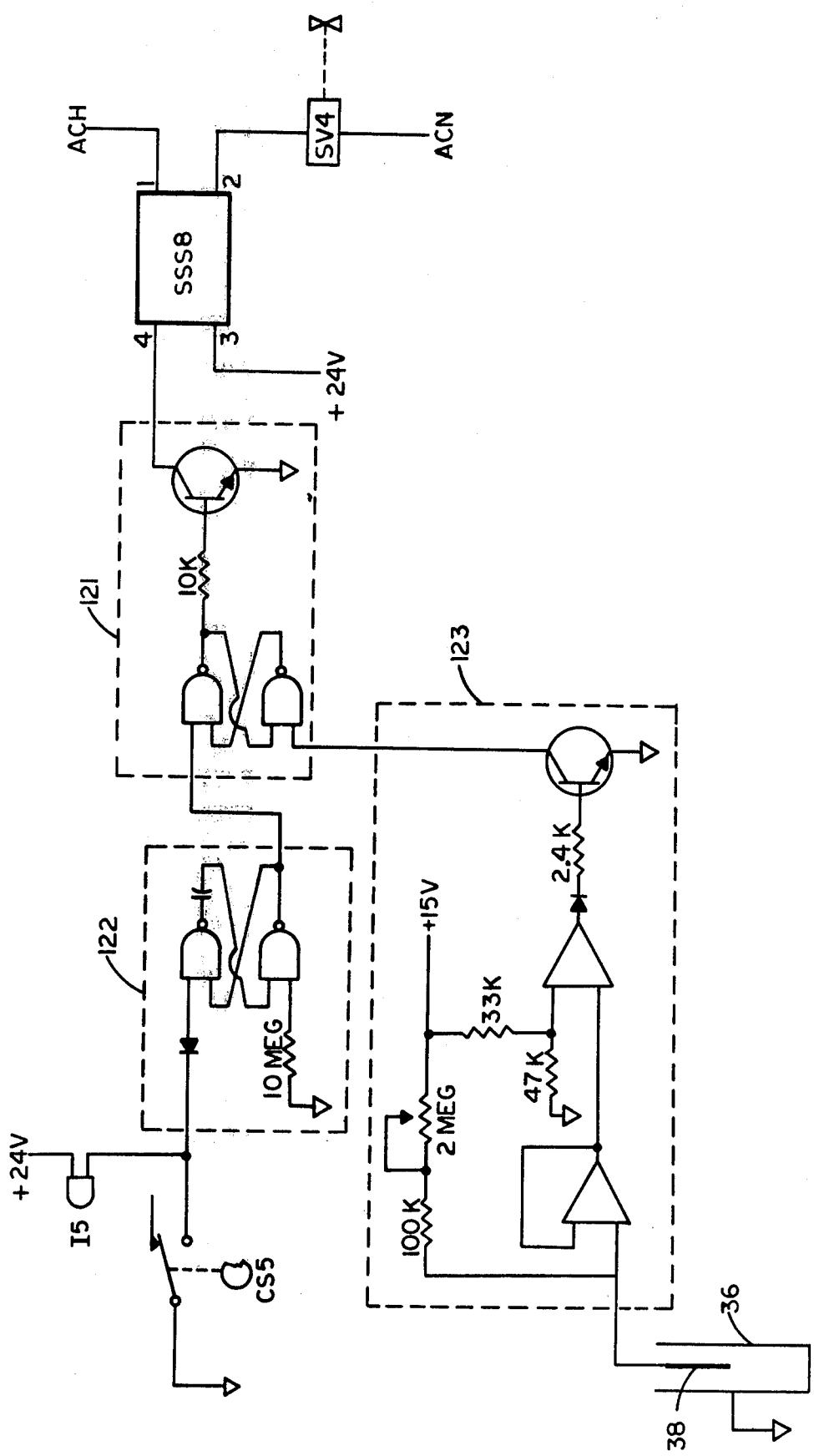
FIG. 17 is a schematic diagram of a sample injection control system.

The sample fill and inject control system is shown in FIG. 17 and includes a solid state switch SSS8 which controls solenoid valve SV4 to turn the three-way valve 35 to connect the reservoir 36 to the waste water weir 42 to fill the reservoir or to the measuring respirometer 15 to deliver a sample of waste water of measured volume to the measuring respirometer 15. The solid state switch SSS8 is driven by a sample "flip-flop" circuit 121 which is set by a "one-shot" circuit 122 which in turn is triggered by sample cam switch CS5 when CS5 enters its dwell. This turns on SSS8 which enables the solenoid valve SV4 to be energized and thereby move three-way valve 35 to connect the reservoir 36 with waste water weir 42 allowing waste water to enter and fill the reservoir. A sample level probe circuit 123 is connected to level detecting probe 38 which extends into the reservoir 36 and to the "flip-flop" circuit 121.

When the waste water level in the reservoir 36 reaches the lower end of probe 38 it connects the sample level probe circuit 123 to ground causing said circuit to reset the "flip-flop" circuit 121 which removes the drive from SSS8 turning it off and de-energizing solenoid valve SV4. De-energization of SV4 causes it to move three-way valve 35 into the position where it connects the reservoir 36 to the measuring respirometer 15 and the measured waste water sample in the reservoir 36 discharges by gravity into the respirometer 15. Provision is made for changing the vertical position of probe 38, as desired, to change the volume of the sample measured by the reservoir 36 to simulate the ratio of influent waste water to mixed liquor in the operation of the actual treatment plant being monitored. This ratio varies from plant to plant and the ability to inject different sample volumes into the measuring respirometer 15 permits closer stimulation of actual conditions in the plant being monitored.

Figure 18:
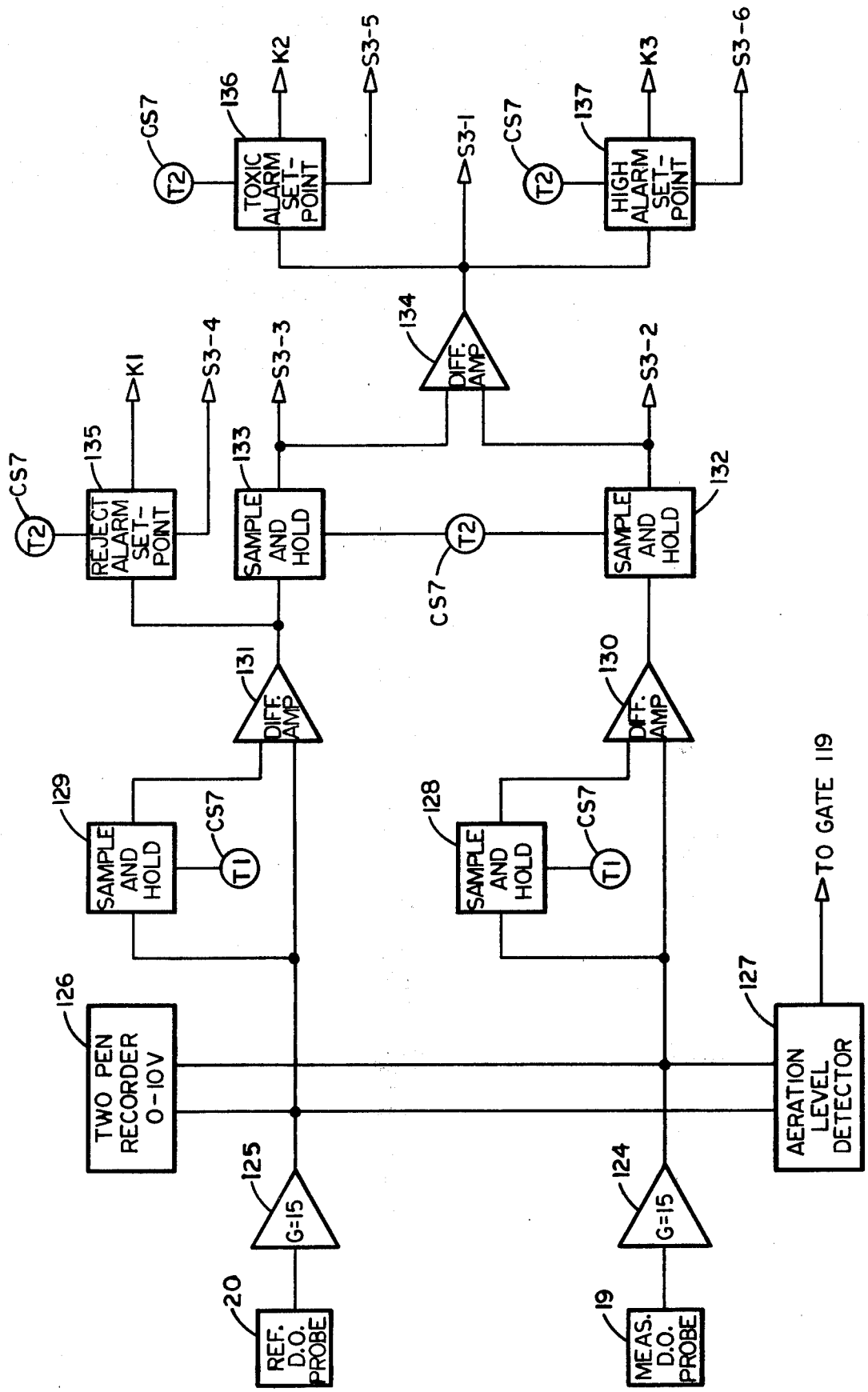
FIG. 18 is a schematic diagram of a signal and alarm system.

Referring now to the Measurement Electronics, FIG. 18 shows the output of the measuring D.O. probe 19 connected to an amplifier 124 which converts the output to a level of one volt equaling one milligram of dissolved oxygen per liter of liquid and shows the output of the reference D.O. probe 20 connected to a second amplifier 125 which converts the output to a level of one volt equaling one milligram of dissolved oxygen per liter of liquid. The signals from amplifiers 124 and 125 are in the 0 to 10 volt range and are used to operate a two-pen recorder 126 and are part of the aeration level detector 127.

A cam timer switch CS7 is diagrammatically illustrated at six places in FIG. 18 for convenience of illustration although only one such switch is provided. After both respirometers 15 and 16 have been filled and aerated and the sample of waste water has been injected into the measuring respirometer 15, the cam timer switch CS7 enters its dwell which begins a time interval starting with T1 and extending to the time T2 when CS7 leaves its dwell. At time T1, when CS7 enters its dwell, the dissolved oxygen level signals from amplifiers 124 (measuring) and 125 (reference) are stored in first and second analog type sample and hold circuits, respectively, 128 (measuring) and 129 (reference) which are also connected to first and second differential amplifiers, respectively, 130 (measuring) and 131 (reference). The dissolved oxygen level signals from amplifiers 124 and 125 are also continuously fed directly to the first and second differential amplifiers 130 and 131, respectively, which continuously output the difference between the dissolved oxygen level at time T1 and at any later time. This difference represents the oxygen uptake in the measuring and reference respirometers 15 and 16 during the interval from time T1 and said any later time. The outputs of differential amplifiers 130 and 131 are connected to third and fourth sample and hold circuits 132 and 133, respectively.

At time T2, when the cam switch CS7 leaves its dwell, the dissolved oxygen level voltages from differential amplifiers 130 and 131 are stored in third and fourth sample and hold circuits 132 and 133, respectively, as M and R, respectively. The outputs of the third and fourth sample and hold circuits 132 and 133 are connected to a third differential amplifier 134 which outputs a voltage representative of the difference (M−R) between the oxygen uptake in the measuring respirometer 15 (M) and the reference respirometer 16 (R) during the time interval T1-T2. The output voltage of the third differential amplifier 134 is also fed to a digital voltmeter (not shown) where it is available for display as M-R via a selector switch S3-1. The voltages stored in the third and fourth sample and hold circuits 132 and 133 are fed to switches S3-2 and S3-3, respectively, where they are available for display as M and R, respectively.

The output voltage of the second differential amplifier 131 is also fed to reject alarm setpoint circuit 135 and the output voltage of the third differential amplifier 134 is also fed to toxic alarm setpoint circuit 136 and high alarm setpoint circuit 137. These three alarm setpoint circuits 135, 136 and 137 are activated at time T2, i.e., when CS7 leaves its dwell, and all three are of the self resetting type. The three alarm setpoint circuits 135, 136 and 137 are connected to alarm relays K1, K2 and K3, respectively.

The reject alarm circuit 135 monitors the oxygen uptake in the reference respirometer 16 and compares it with the setpoint in the circuit. Normally, the mixed liquor in the reference respirometer 16 will have a certain minimal amount of oxygen uptake, but, if the uptake is abnormally low, the reject alarm relay K1 will trip indicating abnormally low uptake in the reference respirometer 16 and provide a visual and/or audible alarm signal. The setpoint in reject alarm setpoint circuit 136 can be adjusted to accommodate different secondary treatment systems and conditions.

The toxic alarm circuit 136 monitors the output voltage representing M−R from the third differential amplifier 134 and compares it with the setpoint in the toxic alarm circuit 136. The toxic alarm relay K2 trips whenever the oxygen uptake (M) in the measuring respirometer 15 equals, or is less than, the oxygen uptake (R) in the reference respirometer 16, i.e., when M−R is 0 or has a negative value, and provides a visual and/or audible alarm signal. The toxic alarm relay K2 can also be connected to actuating circuitry for one or both diversion valves 11, such that tripping of toxic alarm relay K2 also energizes said circuitry to close one or both of said diversion valves from the primary and/or secondary treatment basins 4 and 5, as the case may be, and opens one or both of said valves to the "panic" pond 14.

The high alarm circuit 137 monitors the output voltage representing M−R from the third differential amplifier 134 and compares it with the setpoint in circuit 137. The high alarm relay K3 trips whenever the oxygen uptake (M) in the measuring respirometer 15 is significantly higher than the oxygen uptake (R) in the reference respirometer 16, i.e., when M−R is greater than a preset value, and provides a visual and/or audible alarm signal. The high alarm relay K3 can also be connected to actuating circuitry for one or both diversion valves 11, such that tripping of high alarm relay K3 also energizes said circuitry to close one or both of said valves to the primary and/or secondary treatment basins 4 and 5, as the case may be, and open one or both of said valves to the "panic" pond 14.

The three alarm setpoint circuits 135, 136 and 137 are connected respectively to selector switches S3-4, S3-5 and S3-6 to provide to the digital voltmeter signals representative of the setpoint values in each of the three circuits. The digital voltmeter is provided on the front panel with means to display via pushbutton selector switch S3 (which includes switches S3-1 through S3-6), values of the oxygen uptakes M and R in each respirometer 15 and 16 (the output voltages of the two sample and hold circuits 132 and 133), the differential oxygen uptake $M-R$ (output voltage of the differential amplifier 134), and the setpoints of each of the three alarm circuits.

The sequence of operations of the automated version of the apparatus and method of this invention as shown in FIGS. 11 through 18 is summarized as follows:

1. The glass respirometers 15 and 16 are filled with mixed liquor.
2. Level detecting probes 21 and 22 initiate the closing of the fill valves 25 and 26 automatically when the respirometers are filled to the selected volume.
3. The mixed liquor in the respirometers is stirred and aerated until a dissolved oxygen (D.O.) of at least about six parts per million (ppm) is achieved in both respirometers. An aeration level detector circuit continuously monitors the output of each D.O. probe 19 and 20 and closes the air solenoid valve SV8 when the six ppm D.O. level is attained in both respirometers.
4. After the air has been shut off, a sample of the influent waste water is injected into the measuring respirometer.
5. The mixed liquor in the respirometers 15 and 16 is continuously stirred to ensure total contact between the microorganisms, the waste water sample and the dissolved oxygen.
6. Dissolved oxygen detector probes 19 and 20 simultaneously monitor the oxygen uptake in the measuring and reference respirometers 15 and 16.
7. Electronic circuits automatically convert the uptake slopes of D.O. probes 19 and 20 to output signals. These outputs can be displayed individually by pushbutton signal selector switches on the control panel. The oxygen uptake slopes of the measuring respirometer 15, reference respirometer 16, and the differential $(M-R)$ can be selected for readout on the digital voltmeter. Alarm setpoints can be displayed on the digital voltmeter for three abnormal conditions, toxic, highly degradable, and reject. The analog outputs of the D.O. sensors 19 and 20 are also continuously displayed on a 2-channel strip chart recorder.
8. After the oxygen uptake rates have been measured, the respirometer drain valves 31 and 32 open and the mixed liquor is drained from both respirometers 15 and 16.
9. Then the flush water valve 28 opens and the respirometers 15 and 16 are sprayed internally with flush water for a few seconds, then the drain valves 31 and 32 close and the respirometers completely fill with clean water to wash all residual mixed liquor and sample from the interior surfaces. The stirrers operate during the flush cycle for additional scrubbing action.
10. The drain valves 31 and 32 open again and the flush water is emptied from the respirometers.
11. The stirrers are turned off and a repeat cycle is initiated.

The basic program cycle is about 10 minutes but may be more or less. Additional time is usually required for aeration of the mixed liquor and during the aeration part of the cycle, the cam timer motor 139 is turned off. Depending upon the background respiration of the mixed liquor, the necessary aeration time can vary from one to ten minutes. When the D.O. content reaches six ppm in both respirometers, the program timer is turned on and the remainder of the cycle is completed.

It can be appreciated that the invention provides an improved method and apparatus for monitoring the suitability of waste water influents for secondary treatment by subjecting such influents to conditions simulating as closely as possible those conditions actually existing in the secondary treatment basin and providing alarm signals for toxic conditions, or excessively oxygen depleting conditions, of influents intended for introduction into the basin. The invention also provides for a reject alarm signal when, for some reason, an acceptable oxygen uptake in a control or reference is not obtained. The invention as described provides reliable apparatus and method that can be operated manually or automatically.

Although preferred embodiments of this invention have been described in detail, it will be appreciated that other embodiments are contemplated, along with modifications of the disclosed features, as being within the scope of the invention.

What is claimed is:

1. Method of monitoring a waste influent stream to a waste treatment basin which contains active microorganisms for levels of materials injurious to the microorganisms in the basin comprising the steps of:
   (a) measuring the rate of oxygen uptake, R, in a first sample of liquor from said basin, said first sample having a predetermined volume and a predetermined dissolved oxygen content;
   (b) measuring the rate of oxygen uptake, M, in a mixture of a second sample of liquor taken from said basin and a sample of liquid from said waste influent stream, said second sample having substantially the same volume and dissolved oxygen content as said first sample;
   (c) computing the differential, $M-R$;
   (d) providing a toxic condition signal when said differential, $M-R$, is lower than a predetermined value indicating a toxic effect of said influent stream sample on said sample of liquor from said basin.
   (e) diverting said influent stream to a holding zone separate from said basin, when said differential, $M-R$, is lower than a predetermined value indicating a toxic effect of said influent stream on said sample of liquor from said basin.

2. Method as claimed in claim 1 for also monitoring said influent stream for highly degradable materials capable of causing undue oxygen depletion, bulking or loss of microorganisms in said basin including the step of providing an undue oxygen depletion signal when said differential, $M-R$, is higher than a predetermined value indicating highly degradable material in said influent stream capable of causing undue oxygen depletion, bulking or loss of microorganisms in said sample from said basin.

3. Method as claimed in claim 1 for monitoring the oxygen uptake, R, of said sample of liquor taken from said basin including the step of providing a reject signal when said uptake, R, is less than a predetermined value indicating insufficient oxygen uptake.

4. Method as claimed in claim 3 wherein said influent stream is diverted to a holding zone separate from said basin when said differential, M−R, is higher than a predetermined value indicating highly degradable material in said influent stream capable of causing undue oxygen depletion, bulking or loss of microorganisms in said sample of said basin.

5. Apparatus for monitoring a waste influent stream to a waste treatment basin which contains a mixed liquor containing active microorganisms for levels of materials injurious to said microorganisms in the basin comprising:
(a) means for measuring the rate of oxygen uptake, R, in a sample of liquor from said basin;
(b) means for measuring the rate of oxygen uptake, M, in a mixture of a sample of mixed liquor from said basin and a sample of liquid from said waste influent stream;
(c) means for computing the differential, M−R;
(d) means for providing a toxic alarm signal when said differential, M−R, is lower than a predetermined value indicating a toxic effect of said influent stream sample on said sample of mixed liquor from said basin; and
(e) means for diverting said influent stream to a holding zone separate from said basin, when said differential, M−R, is lower than a predetermined value indicating a toxic effect of said influent stream sample on said sample of mixed liquor from said basin.

6. Apparatus as claimed in claim 5 which includes means for providing an oxygen depletion alarm signal when said differential, M−R, is higher than a predetermined value indicating highly degradable material in said influent stream capable of causing oxygen depletion, bulking or loss of microorganisms in said sample from said basin.

7. Apparatus as claimed in claim 6 which includes means for diverting said influent stream to a holding zone when said differential, M−R, is higher than a predetermined value.

8. Apparatus as claimed in claim 5 which includes means for providing a reject alarm signal when said oxygen uptake, R, of said sample from said basin indicates insufficient oxygen uptake in said sample.

9. Apparatus as claimed in claim 5 which includes:
(a) first and second vessels for receiving first and second measured samples, respectively, of mixed liquor from said basin;
(b) first and second dissolved oxygen detectors operatively connected with the interiors of said first and second vessels, respectively, for measuring the respective dissolved oxygen levels of mixed liquors therein;
(c) means for aerating the first and second samples in said first and second vessels to a predetermined level of dissolved oxygen; and
(d) means for injecting a measured sample of said waste water influent stream into said first vessel.

10. Apparatus as claimed in claim 9 which includes means for stirring the contents of both vessels.

11. Apparatus as claimed in claim 9 which includes valve means for directing mixed liquor from said basin to said first and second vessels.

12. Apparatus as claimed in claim 11 which includes means for detecting a predetermined level of mixed liquor in said first and second vessels.

13. Apparatus as claimed in claim 12 which includes means responsive to said level detecting means for closing said valve means when said predetermined level is reached.

14. Apparatus as claimed in claim 11 wherein said filling means includes a mixed liquor weir through which mixed liquor from said basin continuously flows which said first and second measured samples of mixed liquor is drawn to said first and second vessels.

15. Apparatus as claimed in claim 11 wherein said valve means comprises an inlet port for receiving mixed liquor from said basin, an outlet port for discharging mixed liquor to said forst and second vessels, a first diaphragm movable from a first position allowing mixed liquor to pass from said inlet port to said outlet port to a second position preventing passage of mixed liquor from one port to the other, spring means urging said diaphragm towards one of said positions and a pneumatically actuated driving diaphragm connected to said first diaphragm and acting against said spring means to move said first diaphragm to the other of said positions, when actuated.

16. Apparatus as claimed in claim 9 which includes means for draining said first and second vessels.

17. Apparatus as claimed in claim 9 which includes means for flushing said first and second vessels with flush water.

18. Apparatus as claimed in claim 9 wherein said injecting means includes a measuring vessel in which said sample of waste influent is volumetrically measured and waste water valve means having a first position directing waste water from said stream into said measuring vessel to fill said vessel and a second position directing said waste water sample from said measuring vessel into said first vessel.

19. Apparatus as claimed in claim 18 wherein said measuring vessel is provided with means for detecting a predetermined level of waste water influent therein.

20. Apparatus as claimed in claim 19 which includes means responsive to said waste water level detecting means for actuating said waste water valve means to said second position to direct said waste water sample in the measuring vessel to said first vessel.

21. Apparatus as claimed in claim 19 which includes a waste water weir through which waste water from said influent stream continuously flows and from which waste water is drawn to said waste water valve means.

22. Apparatus as claimed in claim 18 which includes means for flushing said measuring vessel with flush water.

23. Apparatus as claimed in claim 18 wherein said waste water valve means comprises an inlet port for receiving waste water from said influent stream, a measuring vessel port for discharging waste water to said measuring vessel and for receiving waste water from said measuring vessel, an outlet port for discharging waste water to said first and second vessels, a first diaphragm movable from a first position allowing waste water to flow from said waste water stream to said measuring vessel to a second position preventing such flow, a second diaphragm movable from a first position preventing flow of waste water from said measuring vessel to said first vessel to a second position allowing such flow, spring means urging both said diaphragms to their first positions or second positions, and a pneumatically activated driving diaphragm connected to both said first and second diaphragms actingagainst said spring means to move them, when actuated, to the other of their first positions or second positions.

24. Apparatus as claimed in claim 9 which includes means for computing the oxygen uptake rate, M, in said first vessel over a predetermined period of time and means for computing the oxygen uptake rate, R, in said second vessel over the same predetermined period of time.

25. Apparatus as claimed in claim 24 which includes means for providing an undue oxygen depletion signal when said differential $M-R$ is higher than a predetermined value indicating highly degradable material in said influent stream capable of causing undue oxygen depletion, bulking or loss of microorganisms in said sample from said basin.

26. Apparatus as claimed in claim 24 which includes means for providing a reject signal when said uptake R is less than a predetermined value indicating insufficient oxygen uptake in the mixed liquor.

* * * * *

UNITED STATES PATENT AND TRADEMARK OFFICE
CERTIFICATE OF CORRECTION

PATENT NO. : 4,260,490
DATED : April 7, 1981
INVENTOR(S) : Jack R. Moss et al.

It is certified that error appears in the above—identified patent and that said Letters Patent is hereby corrected as shown below:

In the title, change "Biomonotor" to -- Biological Monitor Process and Apparatus --

Inventor "Ronald A. Riemer" should read --Ronald E. Riemer--.

Col. 1, line 1, "Biomonitor" should read --Biological Monitor--.

Col. 5, line 1, "water water" should read --waste water--.

Col. 13, Table - Initial words "Normal", "Toxic", "High", and "Reject" should be underscored.

Col. 16, line 12, "agian" should read --again--.

Col. 16, lines 58 and 62, "and" should be underscored.

Col. 20, line 53, "basin." should read --basin;--

Col. 22, line 19, "forst: should read --first--.

Col. 23, line 5, "actingagainst" should read --acting against--.

Signed and Sealed this

Eighteenth Day of August 1981

[SEAL]

Attest:

GERALD J. MOSSINGHOFF

*Attesting Officer*     *Commissioner of Patents and Trademarks*